United States Patent
Bellotti et al.

(10) Patent No.: US 8,048,015 B2
(45) Date of Patent: *Nov. 1, 2011

(54) METHODS AND APPARATUS FOR CREATING PARTICLE DERIVATIVES OF HDL WITH REDUCED LIPID CONTENT

(75) Inventors: Marc Bellotti, Coto de Caza, CA (US); H. Bryan Brewer, Jr., Potomac, MD (US); Hassibullah Akeefe, San Ramon, CA (US); Adam Paul Conner, Livermore, CA (US); Timothy Jon Perlman, Pleasanton, CA (US)

(73) Assignee: HDL Therapeutics, Shorthills, NJ (US)

( * ) Notice: Subject to any disclaimer, the term of this patent is extended or adjusted under 35 U.S.C. 154(b) by 582 days.

This patent is subject to a terminal disclaimer.

(21) Appl. No.: 12/054,162

(22) Filed: Mar. 24, 2008

(65) Prior Publication Data
US 2008/0234621 A1    Sep. 25, 2008

Related U.S. Application Data

(63) Continuation of application No. 10/796,691, filed on Mar. 8, 2004, now Pat. No. 7,375,191.

(60) Provisional application No. 60/484,690, filed on Jul. 3, 2003.

(51) Int. Cl.
*A61M 1/38* (2006.01)
*A61K 9/14* (2006.01)
*A61K 38/17* (2006.01)
*B01D 11/00* (2006.01)

(52) U.S. Cl. ............ 604/5.03; 514/2; 514/12; 530/359; 424/491; 210/749

(58) Field of Classification Search .................. 604/5.03; 514/2, 12; 530/359; 424/491; 210/749
See application file for complete search history.

(56) References Cited

U.S. PATENT DOCUMENTS

| | | | |
|---|---|---|---|
| 3,647,624 A | 3/1972 | Evenson | |
| 3,958,939 A | 5/1976 | Jones | |
| 3,983,008 A | 9/1976 | Shinozaki et al. | |
| 3,989,466 A | 11/1976 | Pan | |
| 4,025,423 A | 5/1977 | Stonner et al. | |
| 4,103,685 A | 8/1978 | Lupien et al. | |
| 4,124,509 A | 11/1978 | Iijima et al. | |
| 4,234,317 A | 11/1980 | Lucas et al. | |
| 4,235,602 A | 11/1980 | Meyer et al. | |
| 4,258,010 A | 3/1981 | Rozsa et al. | |
| 4,311,586 A | 1/1982 | Baldwin et al. | |
| 4,350,156 A | 9/1982 | Malchesky et al. | |
| 4,391,711 A | 7/1983 | Jackson et al. | |
| 4,399,217 A | 8/1983 | Holmquist et al. | |
| 4,402,940 A | 9/1983 | Nose et al. | |
| 4,435,289 A | 3/1984 | Breslau | |
| 4,463,988 A | 8/1984 | Bouck et al. | |
| 4,481,189 A | 11/1984 | Prince | |
| 4,522,809 A | 6/1985 | Adamowicz et al. | |
| 4,540,401 A | 9/1985 | Marten | |
| 4,540,573 A | 9/1985 | Neurath et al. | |
| 4,591,505 A | 5/1986 | Prince | |
| 4,613,501 A | 9/1986 | Horowitz | |
| 4,615,886 A | 10/1986 | Purcell et al. | |
| 4,643,718 A | 2/1987 | Marten | |
| 4,645,512 A | 2/1987 | Johns | |
| 4,647,280 A | 3/1987 | Maaskant et al. | |
| 4,648,974 A | 3/1987 | Rosskopf et al. | |
| 4,668,398 A | 5/1987 | Silvis | |
| 4,671,909 A | 6/1987 | Torobin | |
| 4,676,905 A | 6/1987 | Nagao et al. | |
| 4,677,057 A | 6/1987 | Curtiss et al. | |
| 4,680,320 A | 7/1987 | Uku et al. | |
| 4,696,670 A | 9/1987 | Ohnishi et al. | |
| 4,775,483 A | 10/1988 | Mookerjea et al. | |
| 4,832,034 A | 5/1989 | Pizziconi et al. | |
| 4,836,928 A | 6/1989 | Aoyagi et al. | |
| 4,879,037 A | 11/1989 | Utzinger | |
| 4,895,558 A | 1/1990 | Cham | |
| 4,908,354 A | 3/1990 | Seidel et al. | |
| 4,909,940 A | 3/1990 | Horowitz et al. | |
| 4,909,942 A | 3/1990 | Sato et al. | |
| 4,923,439 A | 5/1990 | Seidel et al. | |
| 4,935,204 A | 6/1990 | Seidel et al. | |
| 4,966,709 A | 10/1990 | Nose et al. | |
| 4,970,144 A | 11/1990 | Fareed et al. | |
| 5,026,479 A | 6/1991 | Bikson et al. | |
| 5,055,396 A | 10/1991 | Curtiss et al. | |
| 5,080,796 A | 1/1992 | Nose et al. | |
| 5,089,602 A | 2/1992 | Isliker et al. | |
| 5,112,956 A | 5/1992 | Tang et al. | |
| 5,116,307 A | 5/1992 | Collins | |
| 5,126,240 A | 6/1992 | Curtiss | |
| 5,128,318 A | 7/1992 | Levine et al. | |
| 5,152,743 A | 10/1992 | Gorsuch et al. | |
| 5,187,010 A | 2/1993 | Parham et al. | |

(Continued)

FOREIGN PATENT DOCUMENTS

CA    1 271 708    *    7/1990

(Continued)

OTHER PUBLICATIONS

U.S. Appl. No. 12/042,881, filed Mar. 5, 2008, Bellotti et al.*

(Continued)

*Primary Examiner* — Chih-Min Kam
(74) *Attorney, Agent, or Firm* — Kilpatrick Townsend & Stockton LLP

(57) ABSTRACT

The present invention is directed to systems, apparatus and methods for creating derivatives of at least one form of HDL without substantially affecting LDL. These derivatives of HDL are particles with reduced lipid content, particularly reduced cholesterol content. These particles have the capacity to bind cholesterol and are administered to a patient to enhance cellular cholesterol efflux and reduce cholesterol levels in cells, tissues, organs, and blood vessels. The present method is useful for treating atherogenic vascular disease and may be combined with other therapies such as statins, inhibitors of cholesterol absorption, niacin, anti-inflammatories, exercise and dietary restriction.

24 Claims, 21 Drawing Sheets

U.S. PATENT DOCUMENTS

| | | | |
|---|---|---|---|
| 5,203,778 A | 4/1993 | Boehringer et al. |
| 5,211,850 A | 5/1993 | Shettigar et al. |
| 5,236,644 A | 8/1993 | Parham et al. |
| 5,256,767 A | 10/1993 | Salk et al. |
| 5,258,149 A | 11/1993 | Parham et al. |
| 5,279,540 A | 1/1994 | Davidson |
| 5,301,694 A | 4/1994 | Raymond et al. |
| 5,354,262 A | 10/1994 | Boehringer et al. |
| 5,391,143 A | 2/1995 | Kensey |
| 5,393,429 A | 2/1995 | Nakayama et al. |
| 5,401,415 A | 3/1995 | Rauh et al. |
| 5,401,466 A | 3/1995 | Foltz et al. |
| 5,418,061 A | 5/1995 | Parham et al. |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham et al. |
| 5,523,096 A | 6/1996 | Okarma et al. |
| 5,529,933 A | 6/1996 | Young |
| 5,634,893 A | 6/1997 | Rishton |
| 5,637,224 A | 6/1997 | Sirkar et al. |
| 5,652,339 A | 7/1997 | Lerch et al. |
| 5,679,260 A | 10/1997 | Boos et al. |
| 5,698,432 A | 12/1997 | Oxford |
| 5,707,673 A | 1/1998 | Prevost et al. |
| 5,719,194 A | 2/1998 | Mann et al. |
| 5,744,038 A | 4/1998 | Cham |
| 5,753,227 A | 5/1998 | Strahilevitz |
| 5,853,725 A | 12/1998 | Salk et al. |
| 5,855,782 A | 1/1999 | Falkenhagen et al. |
| 5,858,238 A | 1/1999 | McRea et al. |
| 5,877,005 A | 3/1999 | Castor et al. |
| 5,885,578 A | 3/1999 | Salk et al. |
| 5,895,650 A | 4/1999 | Salk et al. |
| 5,911,698 A | 6/1999 | Cham |
| 5,916,806 A | 6/1999 | Salk et al. |
| 5,919,369 A | 7/1999 | Ash |
| 5,928,930 A | 7/1999 | Salk et al. |
| 5,948,441 A | 9/1999 | Lenk et al. |
| 5,962,322 A | 10/1999 | Kozarsky et al. |
| 5,980,478 A | 11/1999 | Gorsuch et al. |
| 6,004,925 A | 12/1999 | Dasseux et al. |
| 6,017,543 A | 1/2000 | Salk et al. |
| 6,022,333 A | 2/2000 | Kensey |
| 6,037,323 A | 3/2000 | Dasseux et al. |
| 6,037,458 A | 3/2000 | Hirai et al. |
| 6,039,946 A | 3/2000 | Strahilevitz |
| 6,046,166 A | 4/2000 | Dasseux et al. |
| 6,080,778 A | 6/2000 | Yankner et al. |
| 6,127,370 A | 10/2000 | Smith et al. |
| 6,136,321 A | 10/2000 | Barrett et al. |
| 6,139,746 A | 10/2000 | Kopf |
| 6,156,727 A | 12/2000 | Garber et al. |
| 6,171,373 B1 | 1/2001 | Park et al. |
| 6,193,891 B1 | 2/2001 | Kent et al. |
| 6,264,623 B1 | 7/2001 | Strahilevitz |
| 6,309,550 B1 | 10/2001 | Iverson et al. |
| 6,337,368 B1 | 1/2002 | Kobayashi et al. |
| RE37,584 E * | 3/2002 | Cham |
| 6,440,387 B1 | 8/2002 | Yankner et al. |
| 6,472,421 B1 | 10/2002 | Wolozin |
| 6,605,588 B1 | 8/2003 | Lees et al. |
| 6,706,008 B2 | 3/2004 | Vishnoi et al. |
| RE39,498 E * | 2/2007 | Cham et al. |
| 7,361,739 B2 | 4/2008 | Bellotti et al. |
| 7,375,191 B2 | 5/2008 | Bellotti et al. |
| 7,393,826 B2 * | 7/2008 | Bellotti et al. |
| 2001/0028895 A1* | 10/2001 | Bisgaier et al. |
| 2002/0055529 A1* | 5/2002 | Bisgaier et al. |
| 2002/0081263 A1* | 6/2002 | Yankner et al. |
| 2002/0107173 A1* | 8/2002 | Friedhoff et al. |
| 2002/0128581 A1 | 9/2002 | Vishnoi et al. |
| 2002/0183379 A1* | 12/2002 | Yankner et al. |
| 2002/0188012 A1* | 12/2002 | Bisgaier et al. |
| 2003/0018013 A1* | 1/2003 | Dasseux et al. |
| 2003/0127390 A1* | 7/2003 | Davis, Jr. |
| 2004/0106556 A1* | 6/2004 | Zhu et al. |
| 2008/0214438 A1* | 9/2008 | Bellotti et al. |
| 2008/0234621 A1* | 9/2008 | Bellotti et al. ............... 604/5.03 |

FOREIGN PATENT DOCUMENTS

| | | | |
|---|---|---|---|
| CN | 1189378 | * | 8/1998 |
| DE | 29 44 138 A1 | * | 6/1981 |
| DE | 31 18 072 A1 | * | 11/1982 |
| DE | 32 13 390 A1 | * | 10/1983 |
| DE | 33 10 263 A1 | * | 9/1984 |
| EP | 0 036 283 A1 | * | 9/1981 |
| EP | 0 267 471 A2 | * | 5/1988 |
| FR | 2 571 971 A1 | * | 4/1986 |
| JP | 127104 | * | 1/1980 |
| JP | 277303 | * | 10/1993 |
| SU | 1116396 A | * | 9/1984 |
| SU | 1204224 A | * | 1/1986 |
| SU | 1752187 | * | 12/1990 |
| WO | WO 8809345 | * | 12/1988 |
| WO | WO 95/03840 A1 | * | 2/1995 |
| WO | WO 99/38498 A1 | * | 8/1999 |
| WO | WO 01/45718 A1 | | 6/2001 |
| WO | WO 01/56579 A1 | | 8/2001 |
| WO | 02/00266 A2 | | 1/2002 |
| WO | WO 02/10768 A3 | | 2/2002 |
| WO | WO 02/30863 A2 | | 4/2002 |
| WO | WO 02/062824 A2 | | 8/2002 |
| WO | 03/000372 A2 | | 1/2003 |
| WO | WO 03/000373 A1 | | 1/2003 |

OTHER PUBLICATIONS

U.S. Appl. No. 12/054,088, filed Mar. 24, 2008, Bellotti et al.*
U.S. Appl. No. 12/203,551, filed Sep. 3, 2008, Zhu et al.*
Agnese et al., Evaluation of Four Reagents for Delipidation of Serum, *Clinical Biochemistry*, v. 16, 98-100 (1983).
Albouz et al., Extraction of Plasma Lipids Preserving Antigenic Properties of Proteins and Allowing Quantitation of Gangliosides by Neuraminic Acid Determination, *Ann. Biol. Clin.*, v. 37, 287-290 (abstract only) (1979).
André et al., Characterization of Low- and Very-Low-Density Hepatitis C Virus RNA-Containing Particles, *Journal of Virology*, v. 76, 6919-6928 (Jul. 2002).
Asztalos et al., Distribution of Apo A-I-Containing HDL Subpopulations in Patients with Coronary Heart Disease, *Arteriosclerosis, Thrombosis, and Vascular Biology*, v. 20, 2670-2676 (Dec. 2000).
Asztalos et al., Role of Free Apolipoprotein A-I in Cholesterol Efflux, *Arteriosclerosis, Thrombosis, and Vascular Biology*, v. 17, 1630-1636, (1997).
Asztalos et al., Presence and Formation of Free Apolipoprotein A-I-Like Particles in Human Plasma, *Arteriosclerosis, Thrombosis, and Vascular Biology*, v. 15, 1419-1423, (1995).
Badimon et al., Regression of Atherosclerotic Lesions by High Density Lipoprotein Plasma Fraction in the Cholesterol-Fed Rabbit, *J. Clinical Investigation*, v. 85, 1234-1241 (1990).
Badimon et al., High Density Lipoprotein Plasma Fractions Inhibit Aortic Fatty Streaks in Cholesterol-Fed Rabbits, *Laboratory Investigation*, v. 60, 455-461 (1989).
Barrans et al., Hepatic Lipase Induces the formation of pre-beta 1 high density lipoprotein (HDL) from triacylglycerol-rich HDL2 A study comparing liver perfusion to in vitro incubation with lipases, *J. Biol. Chem.*, v. 269, 11572-11577 (1994).
Barrans et al., Pre-β HDL, Structure and Metabolism, *Biochimica et Biophysica Acta—Lipids and Lipid Metabolism*, v. 1300, 73-85 (1996).
Barres et al., Cholesterol—Making or Breaking the Synapse, *Science*, v. 294, 1296-1297 (1996).
Blanche et al., Characterization of Complexes of Egg Yolk Phosphatidylcholine and Apolipoprotein A-II Prepared in Absence and Presence of Sodium Cholate, *Biochimica et Biophysica Acta*, v. 958, 143-152 (1988).
Bloom et al., Quantitation of lipid profiles from isolated serum lipoproteins using small volumes of human serum, *Clin. Biochem.*, v. 14, 119-125 (abstract only) (Jun. 1981).
Burns et al., Use of In Vivo Models to Study the Role of Cholesterol in the Etiology of Alzheimer's Disease, *Neurochem. Res.*, v. 28, 979-86 (abstract only) (Jul. 2003).

Calero et al., Functional and Structural Properties of Lipid-Associated Apolipoprotein J (Clusterin), *Biochemical Journal*, v. 344, 375-383 (1999.

Cham, Nature of the Interaction Between Low-Density Lipoproteins and Polyanions and Metal as Exemplified by Heparin and $Ca^{2+}$, *Clinical Chemistry*,. v. 22, 1812-1816 (1976).

Cham et al., 59th Congress European Atherosclerosis Society, Nice, France, Rapid Regression of Atherosclerosis by Cholesterol Apheresis—A Newly Developed Technique, 17-21. (abstract only) (May 1992).

Cham et al., Heterogeneity of Lipoprotein B, *Biochemical and Biophysical Research Communications*, v. 103, 196-206 (1981).

Cham et al., Importance of Apolipoproteins in Lipid Metabolism, *Chem. Biol. Interactions*, v. 20, 263-277 (1978).

Cham et al., Rapid, Sensitive Method for the Separation of Free Cholesterol from Ester Cholesterol, *Clinica Chimica Acta*, v. 49, 109-113 (1973).

Cham et al., Changes in Electrophoretic Mobilities of α- and β-Lipoproteins as a Result of Plasma Delipidation, *Clinical Chemistry*, v. 22, 305-309. (1976).

Cham et al., *Clinical Chemistry*, Phospholipids in EDTA—Treated Plasma and Serum, v. 39, 2347-2348. (1993).

Cham et al., In Vitro Partial Relipidation of Apolipoproteins in Plasma, *J. Biol. Chem.*, v. 251, 6367-6371. (abstract only) (1976).

Cham et al., Lipid Apheresis in an Animal Model Causes In Vivo Changes in Lipoprotein Electrophoretic Patterns, *J. Clin. Apheresis*, v. 11, 61-70. (1996).

Cham et al., Lipid Apheresis, An In Vivo Application of Plasma Delipidation with Organic Solvents Resulting in Acute Transient Reduction of Circulating Plasma Lipids in Animals, *J. Clin. Apheresis*, v. 10,61-69. (1995).

Cham et al., a Solvent System for Delipidation of Plasma or Serum Without Protein Precipitation, *J. of Lipid Research*, v. 17, 176-181. (1976).

Cham et al., Lipid Apheresis in an Animal Model Causes Acute Reduction in plasma Lipid Concentrations and Mobilisation of Lipid from Liver and Aorta, *Pharmacol. (Life Sci. Adv.)*, v. 13, 25-32 (1994).

Clay, et. al., Formation of apolipoprotein-specific high-density lipoprotein particles from lipid-free apolipoproteins A-I and A-II, *Biochem. J.*, 337, 445-451 (1999).

Collet et al., Differential Effects of Lecithin and Cholesterol on the Immunoreactivity and Confirmation of Apolipoprotein A-I in High Density Lipoproteins, *Journal of Biological Chemistry*, v. 266(14), 9145-9152 (May 15, 1991).

Cooper, Dietary Lipids in the Aetiology of Alzheimer s Disease: Implications for Therapy , *Drugs Aging*, v. 20(6), 399-418 (abstract only) (2003).

Cruzado et al., Characterization and Quantitation of the Apoproteins of High-Density Lipoprotein by Capillary Electrophoresis, *Analytical Biochemistry*, v. 243, Article No. 0487, pp. 100-109 (1996).

Dass et al., Apolipoprotein A-1, Phospholipid Vesicles, and Cyclodextrins as Potential Anti-Atherosclerotic Drugs: Delivery, Pharmacokinetics, and Efficacy, *Drug Delivery*, v. 7, 161-182, (2000).

Deva et al., Establishment of an in-use testing method for evaluating disinfection of surgical instruments using the duck hepatitis B model , *J. Hosp. Infect.*, v. 22, 119-130. (abstract only) (Jun. 1996).

Durbin et al., The Effect of Apolipoprotein A-II on the Structure and Function of Apolipoprotein A-I in a Homogeneous Reconstituted High Density Lipoprotein Particle, *The Journal of Biological Chemistry*, v. 272(50), 31333-31339.

Durbin et. al, Lipid-free apolipoproteins A-I and A-II Promote Remodeling of Reconstituted High Density Lipoproteins and Altar their Reactivity with Lecithin: Cholesterol Acyltransferase, *Journal of Lipid Research*, v. 40(12), 2293-302 (1999).

Dwivedy, 18th Australian Atherosclerosis Society Conference, Gold Coast, Australia, Increase of Reverse Cholesterol Transport by Cholesterol Apheresis Regression of Atherosclerosis, (1992).

Eisenhauer et al., Selective Removal of Density Lipoproteins (LDL) by Precipitation at Low pH: First Clinical Application of the HELP System, *Klin Wochenschr (KWH)*, v. 65, 161-168. (1987).

Fang et al., 18th Australian Atherosclerosis Society Conference, Gold Coast, Australia, In Vivo Rapid Mobilization of Adipose Tissue by Lipid Apheresis—A Newly Developed Technique, (1992).

Feinstone et al., Inactivation of Hepatits B Virus and Non-A, Non-B Hepatitis by Chloroform, *Infection and Immunity*, v. 41, 816-821 (Aug. 1983).

Gasparini et al., Peripheral Markers in Testing Pathophysiological Hypotheses and Diagnosing Alzheimer s Disease, *FASEB J.*, v. 12, 17-34 (1998).

Gauthier et al., Alzheimer s Disease: Current Kowledge, Management and Research, *Can. Med.Assoc. J.*, v. 157(8), 1047-1052 (1997).

Golde et al., Cholesterol Modulation as an Emerging Strategy for the Treatment of Alzheimer s Disease, *Drug Discovery Today*, v. 6(20), 1049-1055 (abstract only) (Oct. 15, 2001).

Greicius et al., Presenile Dementia Syndrome: An Update on Taxonomy and Diagnosis, *Journal of Neurol. Neurosurg. Psychiatry*. v. 72, 691-700 (2002).

Haas et al., Apolipoprotein E Forms Stable Complexes with Recombinant Alzheimer s Disease Beta-Amyloid Precursor Protein, *Biochemical Journal*, v. 325, 169-175 (1997).

Hatch et al., Practical Methods for Plasma Lipoprotein Analysis, *Advances in Lipid Research*, v. 6, 61-68 (1968).

Horowitz et al., Viral safety of solvent/detergent-treated blood products, *Blood Coagulation and Fibrinolysis*, v. 5, S21-S28 (1994).

Innerarity et al., Enhanced Binding by Cultured Human Fibroblasts of Apo-E-Containing Lipoproteins as Compared with Low Density Lipoproteins, *Biochemistry*, v. 17, 1440-1447 (1978).

Ito et al., Cholesterol-Sphingomyelin Interaction in Membrane and Apolipoprotein-Mediated Cellular Cholesterol Efflux, *Journal of Lipid Research*, v. 41, 894-904 (2001).

Jackson et al., Isolation and Characterization of the Major Apolipoprotein from Chicken High Density Lipoproteins, *Biochimica et Biophysica Acta*, v. 420, 342-349 (1976).

Klimov et al., Extraction of Lipids from Blood Plasma and Subsequent Introduction of Autologous Delipidized Plasma into the Body as a Possible Means to Treat Atherosclerosis [translation], *Kardologiia*, v. 18, 23-29 (1978).

Koizumi et al., Behavior of Human Apolipoprotein A-1: Phospho-Lipid and apoHDL: Phospholipid Complexes In Vitro and After Injection into Rabbits, *J. Lipid Research*, v. 29, 1405-1415 (1988).

Kostner, Beyond LDL-Cholesterol or Enhancing Reverse Cholesterol Transport, *Journal für Kardiologie*, No. 7-8, 328-331 (2002).

Kostner et al., Lecithin-cholesterol acyltransferase activity in Normocholesterolaemic and Hypercholesterolaemic Roosters: Modulation by Lipid Apheresis, *European Journal of Clinical Investigation*, v. 27, 212-218 (May 7, 1997).

Kostner et al., XI Internet Symp. on Drugs Affecting Lipid Metabolism, Italy, Increase of APO A1 Concentration in Hypercholesteraemic Chickens after Treatment with a Newly Developed Extracorpreal Lipid Elimination (May 13, 1992).

Koudinov et al., Biochemical Characterization of Alzheimer s Soluble Amyloid Beta Protein in Human Cerebrospinal Fluid: Association with High Density Lipoproteins, *Biochem. Biophys. Res. Commun.*, v. 223(3), 592-7 (abstract only) (Jun. 25, 1999).

Koudinov et al., Cell Biol Int, Alzheimer s Soluble Amyloid Beta Protein is Secreted by HepG2 Cells as an Apolipoprotein, v. 21(5), 265-71 (abstract only) (May 1997).

Koudinov et al., Alzheimer s Amyloid Beta Interaction with Normal Human Plasma High Density Lipoprotein: Association with Apolipoprotein and Lipids, *Clin. Chim. Acta*, v. 270(2), 75-84 (abstract only) (Feb. 23, 1999).

Koudinov et al., Cholesterol s Role in Synapse Formation, *Science*, v. 294, 2213 (Nov. 9, 2001).

Koudinova et al., Amyloid Beta, Neural Lipids, Cholesterol and Alzheimer s Disease—Abstract No. 2110, *Soc. Neuroscience. Abstract Viewer and Itinerary Planner*, (2002).

Kunitake et al., Interconversion between Apolipoprotein A-I-containing Lipoproteins of Pre-beta and Alpha Electrophoretic Mobilities, *J. Lipid Res.*, v. 33(12), 1807-1816 (1992).

Ladu et al., Association of Human, Rat, and Rabbit Apolipoprotein E with Beta-Amyloid, *Journal of Neuroscience Research*, v. 49(1), 9-18, (1997).

Lipid Sciences, http://wwwlipidsciencescom/technologyhtml, Lipid Technology, 1-4 (Aug. 25, 2001).

Lupien et al., A New Approach to the Management of Familial Hypercholesterolaemia: Removal of Plasma-Cholesterol Based on the Principle of Affinity Chromatography, *Lancet*, v. 307(7972), 1261-1265, (1976).

Matz et al., Reaction of Human Lecithin Cholesterol Acyltransferase with Synthetic Micellar Complexes of Apolipoprotein A-1, Phosphatidylcholine, and Cholesterol, *The Journal of Biological Chemistry*, v. 257, 4541-4546 (1982).

Mauch et al., CNS Synaptogenesis Promoted by Glia-Derived Cholesterol, *Science*, v. 294, 1354-1357 (Nov. 9, 2001).

Moya et al., A Cell Culture System for Screening Human Serum for Ability to Promote Cellular Cholesterol Efflux, *Arteriosclerosis and Thrombosis*, v. 14(7), 1056-1065 (Jul. 1994).

Nakawatase et al., *Alzheimer s Disease and Related Dementias*, Cecil's Textbook of Medicine (Twenty-First Edition, vol. 1) WB Saunders Company, 2042-2045 (2000).

Ngu, Chronic Infections from the Perspective of Evolution: a Hypothesis, *Medical Hypotheses*, v. 42, 81-88 (1994).

Ngu, Human Cancers and Viruses: A Hypothesis for Immune Destruction of Tumours Caused by Certain Enveloped Viruses Using Modified Viral Antigens, *Medical Hypotheses*, v. 39, 17-21 (1992).

Ngu, The viral envelope in the evolution of HIV: a hypothetical approach to inducing an effective immune response to the virus, *Medical Hypotheses*, v. 48, 517-521 (1997).

Nissen et al., Effect of Recombinant ApoA-1 Milano on Coronary Atherosclerosis in Patients with Acute Coronary syndromes, *Journal of American Medical Association*, v. 290, 2292-2300 (2003).

Okazaki et al., Improved High-Performance Liquid Chromatographic Method for the Determination of Apolipoproteins in Serum High-Density Lipoproteins, *Journal of Chromatography, Biomedical Applications*, v. 430, 135-142 (1988).

Osborne et al., Delipidation of Plasma Lipoproteins, *Methods in Enzymology*, v. 128, 213-222. (1986).

Parker et al., Plasma High Density Lipoprotein is Increased in Man When Low Density Lipoprotein (LDL) is Lowered by LDL-Pheresis, *Proceedings of the National Academy of Sciences*, v. 83, 777-781 (1986).

Refolo et al., Cholesterol Metabolism: A Potential Target for Alzheimer s Disease Therapy, *Soc. Neuroscience Abstracts*, v. 27(2), 1518 (abstract only) (2001).

Robern, The Application of Sodium Deoxycholate and Sephacryl-200 for the Delipidation and Separation of High Density Lipoprotein, *Experientia*, v. 38, 437-439 (1982).

Paternò et al., Reconstituted High-Density Lipoprotein Exhibits Neuroprotection in Two Rat Models of Stroke, *Cerebrovascular Diseases*, v. 17, 204-211 (2004).

Ryan et al., An Improved Extraction Procedure for the Determination of Triglycerides and Cholesterol in Plasma or Serum, *Clinical Chemistry*, v. 13, 769-772 (1967).

Rye et al., Changes in the Size of Reconstituted High Density Lipoproteins during Incubation with Cholesteryl Ester transfer protein: the Role of Apolipoproteins, *Journal of Lipid Research*, v. 33, 215-224 (1992).

Scanu et al., Solubility in Aqueous Solutions of Ethanol of the Small Molecular Weight Peptides of the Serum Very Low Density and High Density Lipoproteins: Relevance to the Recovery Problem During Delipidation of Serum Lipoproteins, *Analytical Biochemistry*, v. 44, 576-588 (1971).

Segrest et al., A Detailed Molecular Belt Model for Apolipoprotein A-I in Discoidal High Density Lipoprotein, *The Journal of Biological Chemistry*, v. 274(45), 31755-31758, (Nov. 5, 1999).

Simons et al., Cholesterol and Alzheimer s Disease: Is There a Link? *Neurology*, v. 57, 1089-1093 (2001).

Slater et al., The Effect of Delipidated High Density Lipoprotein on Human Leukocyte Sterol Synthesis, *Atherosclerosis*, v. 35, 41-49 (1980).

Slater et al., A Comparison of Delipidated Sera Used in Studies of Sterol Synthesis by Human Mononuclear Leukocytes, *J. of Lipid Research*, v. 20, 413-416 (1979).

Sviridov et al., Dynamics of Reverse Cholesterol Transport: Protection against Atherosclerosis, *Atherosclerosis*, v. 161(2), 245-254 (Apr. 2002).

Tadey et al., Chromatographic Techniques for the Isolation and Purification of Lipoproteins, *Journal of Chromatography B*, v. 671, 237-253 (1995).

Thompson et al., Plasma Exchange in the Management of Homozygous Familial Hypercholesterolaemia, *Lancet*, v. 305(7918), 1208-1211 (1975).

Tricerri et al., Interaction of Apolipoprotein A-1 in Three Different Conformations with Palmitoyl Oleoyl Phosphatidylcholine Vesicles, *Journal of Lipid Research*, v 43, 187-197 (2002).

Walker et al., Escape from Immune System, *Nature*, v. 407, 313-314 (2000).

Williams et al., Low Density Lipoprotein Receptor-Independent Hepatic Uptake of a Synthetic, Cholesterol-Scavenging Lipoprotein: Implications for the Treatment of Receptor-Deficient Atherosclerosis, *Proc. Natl. Acad. Sci. USA*, v. 85, 242-246 (1988).

Williams et al., Uptake of Endogenous Cholesterol by a Synthetic Lipoprotein, *Biochim Biophys Acta*, v. 875(2), 183-194 (Feb. 12, 1986).

Wong et al., Retention of gangliosides in serum delipidated by diisopropyl ether-1-butanol extraction, *Journal of Lipid Research*, v. 24, 666-669 (1983).

Wormser, Henry, Lipids, Slide Presentation—PSC 3110, Fall Semester 2002.

Yokoyama et al., Selective Removal of Low Density Lipoprotein by Plasmapheresis in Familial Hypercholesterolemia, *Arteriosclerosis*, v. 5, 613-622 (1985).

Yoshidome et al. Serum Amyloid A and P Protein Levels are Lowered by Dextran Sulfate Cellulose Low-Density Lipoprotein Apheresis, *Artif. Organs*, v. 22(2), 144-148 (1998).

Zetia, http://wwwzetiacom/ezetimbe/zetia/hcp/product_highlights/indexjsp, Zetia (ezetimibe), 1-2 (Aug. 18, 2003).

Zetia, http://wwwzetiacom/ezetimibe/zetiahcp/mechanism_of_action/indexjsp, Zetia: Compliments Statin with a Unique Mechanism, 1-2 (Aug. 18, 2003).

Zhang et al., Characterization of Phospholipids in pre-α HDL: Selective Phospholipid Efflux with Apolipoprotein A-I, *Journal of Lipid Research*, v. 39, 1601-1607 (1998).

\* cited by examiner

Normal Plasma FPLC Profile

ApoA1 vs. Phospholipid FPLC Profile for 100% DIPE Delipidation Method
For Treatment of the Normal Plasma Pool Superose 6 FPLC Profile of Normal Plasma Superose 6 FPLC Profile of Normal Plasma
Treated with 100% DIPE Superose 6 FPLC Profile of Normal Plasma Treated with a Solvent Ratio of 95:5 Sevoflurane to n-Butanol Superose 6 FPLC Profile of Normal Plasma Treated with a Solvent Ratio of 75:25 DIPE to n-Butanol Superose 6 FPLC Profile of Normal Plasma Treated with a
Solvent Ratio of 95:5 DIPE to n-Butanol ApoA-I-containing HDL subspecies determined by 3-16% native PAGE, immunoblot, and image analyses ApoA-I-containing HDL subspecies determined by 3-16% native PAGE, immunoblot, and image analyses

1900

US 8,048,015 B2

METHODS AND APPARATUS FOR CREATING PARTICLE DERIVATIVES OF HDL WITH REDUCED LIPID CONTENT

PRIOR RELATED APPLICATIONS

This application is a continuation application of U.S. patent application Ser. No. 10/796,691, filed Mar. 8, 2004, now issued as U.S. Pat. No. 7,375,191, which claims the benefit of priority to U.S. provisional patent application Ser. No. 60/484,690, filed Jul. 3, 2003, each herein incorporated by reference in its entirety.

FIELD OF INVENTION

The present invention generally relates to systems, apparatus and methods for removing lipids from HDL particles while leaving LDL particles substantially intact, via the extracorporeal treatment of blood plasma using either a single solvent or multiple solvents. The method of the present invention provides a procedure for selective removal of lipid from HDL to create a modified HDL particle while leaving LDL particles substantially intact. The method of the present invention provides a procedure for removing LDL particles from plasma before treating the HDL particles to remove lipid. This invention creates particles comprising derivatives of HDL that may be administered to an animal or human for therapeutic use such as treatment of arteriosclerosis and atherosclerotic vascular diseases within an animal or human.

BACKGROUND

Introduction—Hyperlipidemia and Arteriosclerosis

Cardiovascular, cerebrovascular, and peripheral vascular diseases are responsible for a significant number of deaths annually in many industrialized countries. One of the most common pathological processes underlying these diseases is arteriosclerosis. Arteriosclerosis is characterized by lesions, which begin as localized fatty thickenings in the inner aspects of blood vessels supplying blood to the heart, brain, and other organs and tissues throughout the body. Over time, these atherosclerotic lesions may ulcerate, exposing fatty plaque deposits that may break away and embolize within the circulation. Atherosclerotic lesions obstruct the lumens of the affected blood vessels and often reduce the blood flow within the blood vessels, which may result in ischemia of the tissue supplied by the blood vessel. Embolization of atherosclerotic plaques may produce acute obstruction and ischemia in distal blood vessels. Such ischemia, whether prolonged or acute, may result in a heart attack or stroke from which the patient may or may not recover. Similar ischemia in an artery supplying an extremity may result in gangrene requiring amputation of the extremity.

For some time, the medical community has recognized the relationship between arteriosclerosis and levels of dietary lipid, serum cholesterol, and serum triglycerides within a patient's blood stream. Many epidemiological studies have been conducted revealing that the amount of serum cholesterol within a patient's blood stream is a significant predictor of coronary disease. Similarly, the medical community has recognized the relationship between hyperlipidemia and insulin resistance, which can lead to diabetes mellitus. Further, hyperlipidemia and arteriosclerosis have been identified as being related to other major health problems, such as obesity and hypertension.

Cholesterol Transport

Cholesterol circulating in the blood is carried by plasma lipoproteins that transport lipids throughout the blood. The plasma lipoproteins are classified in five types according to size: chylomicrons (which are largest in size and lowest in density), very low-density lipoproteins (VLDL), intermediate density lipoproteins (IDL), low-density lipoproteins (LDL), and high-density lipoproteins (HDL) (which are the smallest and most dense). These plasma lipoproteins exhibit differences in size, density, diameter, protein content, phospholipid content and triacylglycerol content, known to one of ordinary skill in the art. Of these, the low-density lipoprotein (LDL) and high-density lipoprotein (HDL) are primarily the major cholesterol carrier proteins. The protein component of LDL, the apolipoprotein-B (Apo B) and its products comprise the atherogenic elements. Elevated plasma LDL levels and reduced HDL levels are recognized as the primary cause of coronary disease because Apo B is in highest concentration in LDL particles and is not present in HDL particles. Apolipoprotein A-1 (Apo A-1) and apolipoprotein A-2 (Apo A-2) are found in HDL. Other apolipoproteins, such as Apo C and its subtypes (C-1, C-2 and C-3), Apo D and Apo E are also found in HDL. Apo C and Apo E are also observed in LDL particles.

Numerous major classes of HDL particles including $HDL_{2b}$, $HDL_{2a}$, $HDL_{3a}$, $HDL_{3b}$ and $HDL_{3c}$ have been reported (Segrest et al., Curr. Opin. Lipidol. 11:105-115, 2000). Various forms of LDL particles have been described on the basis of electrophoretic mobility on agarose as two major populations, a major fraction with $\alpha$-HDL mobility and a minor fraction with migration similar to VLDL (Barrans et al., Biochemica Biophysica Acta 1300; 73-85, 1996). This latter fraction has been called pre-$\beta$ HDL and these particles are thought to be the most efficient HDL particle subclass for inducing cellular cholesterol efflux (Segrest et al., Curr. Opin. Lipidol. 11:105-115, 2000). The pre-$\beta$ HDL particles have been further separated into pre-$\beta_1$ HDL, pre-$\beta_2$ HDL and pre-$\beta_3$ HDL. These lipoprotein particles are comprised of Apo A-1, phospholipids and free cholesterol. The pre-$\beta$ HDL particles are considered to be the first acceptors of cellular free cholesterol and are essential in eventually transferring free and esterified cholesterol to $\alpha$-HDL (Barrans et al., Biochemica Biophysica Acta 1300; 73-85, 1996). Pre-$\beta_3$ HDL particles may transfer cholesterol to $\alpha$-HDL or be converted to $\alpha$-HDL. These pre-$\beta$ HDL particles have been characterized in terms of their charge, molecular mass (ranging from 40 kDa-420 kDa), size (Stoke's radius 4 nm-15 nm), shape (ellipsoidal, discoidal or spherical) and chemical composition (protein (including Apo A-1), free cholesterol, esterified cholesterol, phospholipids and the ratio of free cholesterol to phospholipids (see Barrans et al., Biochemica Biophysica Acta 1300; 73-85, 1996 for additional details)). HDL levels are inversely correlated with atherosclerosis and coronary artery disease. Accordingly, what is needed is a method to decrease or remove cholesterol from these various HDL particles, especially the pre-$\beta$ HDL particles, so that they are available to remove additional cholesterol from cells.

Cholesterol is synthesized by the liver or obtained from dietary sources. LDL is responsible for transferring cholesterol from the liver to tissues at different sites in the body. However, if LDL collects on the arterial walls, it undergoes oxidation caused by oxygen free radicals liberated from the body's chemical processes and interacts deleteriously with the blood vessels. The modified LDL causes white blood cells in the immune system to gather at the arterial walls, forming a fatty substance called plaque and injuring cellular layers that line blood vessels. The modified oxidized LDL also reduces the level of nitric oxide, which is responsible for relaxing the blood vessels and thereby allowing the blood to flow freely. As this process continues, the arterial walls slowly constrict, resulting in hardening of the arteries and thereby reducing blood flow. The gradual build-up of plaque can result in blockage of a coronary vessel and ultimately in a heart attack.

In contrast to LDL, high plasma HDL levels are desirable because they play a major role in "reverse cholesterol transport", where the excess cholesterol is transferred from tissue sites to the liver where it is catabolized and eliminated. Optimal total cholesterol levels are 200 mg/dl or below with a LDL cholesterol level of 160 mg/dl or below and a HDL-cholesterol level of 45 mg/dl for men and 50 mg/dl for women. Lower LDL levels are recommended for individuals with a history of elevated cholesterol, atherosclerosis or coronary artery disease.

Current Methods of Treatment

Hyperlipidemia may be treated by changing a patient's diet. However, diet as a primary mode of therapy requires a major effort on the part of patients, physicians, nutritionists, dietitians, and other health care professionals and thus undesirably taxes the resources of health professionals. Another negative aspect of this therapy is that its success does not rest exclusively on diet. Rather, success of dietary therapy depends upon a combination of social, psychological, economic, and behavioral factors. Thus, therapy based only on correcting flaws within a patient's diet is not always successful.

In instances when dietary modification has been unsuccessful, drug therapy has been used as an alternative. Such therapy has included use of commercially available hypolipidemic drugs administered alone or in combination with other therapies as a supplement to dietary control. These drugs, called statins, include natural statins, lovastatin, pravastatin, simvastatin, fluvastatin, atorvastatin, and cerivastatin. Statins are particularly effective for lowering LDL levels and are also effective in the reduction of triglycerides, apparently in direct proportion to their LDL-lowering effects. Statins raise HDL levels, but to a lesser extent than other anti-cholesterol drugs. Statins also increase nitric oxide, which, as described above, is reduced in the presence of oxidized LDL.

Bile acid resins, another drug therapy, work by binding with bile acid, a substance made by the liver using cholesterol as one of the primary manufacturing components. Because the drugs bind with bile acids in the digestive tract, they are then excreted with the feces rather than being absorbed into the body. The liver, as a result, must take more cholesterol from the circulation to continue constructing bile acids, resulting in an overall decrease in LDL levels.

Nicotinic acid, or niacin, is also known as vitamin $B_3$. It is extremely effective in reducing triglyceride levels and raising HDL levels higher than any other anti-cholesterol drug. Nicotinic acid also lowers LDL-cholesterol.

Fibric acid derivatives, or fibrates, are used to lower triglyceride levels and increase HDL when other drugs ordinarily used for these purposes, such as niacin, are not effective.

Probucol lowers LDL-cholesterol levels, however, it also lowers HDL levels. It is generally used for certain genetic disorders that cause high cholesterol levels, or in cases where other cholesterol-lowering drugs are ineffective or cannot be used.

Hypolipidemic drugs have had varying degrees of success in reducing blood lipid; however, none of the hypolipidemic drugs successfully treats all types of hyperlipidemia. While some hypolipidemic drugs have been fairly successful, the medical community has not found any conclusive evidence that hypolipidemic drugs cause regression of atherosclerosis.

In addition, all hypolipidemic drugs have undesirable side effects. As a result of the lack of success of dietary control, drug therapy and other therapies, atherosclerosis remains a major cause of death in many parts of the world.

New therapies have been used to reduce the amount of lipid in patients for whom drug and diet therapies were not sufficiently effective. For example, extracorporeal procedures like plasmapheresis and LDL-apheresis have been employed and are shown to be effective in lowering LDL.

Plasmapheresis therapy or plasma exchange therapy, involves replacing a patient's plasma with donor plasma or more usually a plasma protein fraction. Plasmapheresis is a process whereby the blood plasma is removed from blood cells by a cell separator. The separator works either by spinning the blood at high speed to separate the cells from the fluid or by passing the blood through a membrane with pores so small that only the fluid component of the blood can pass through. The cells are returned to the person undergoing treatment, while the plasma is discarded and replaced with other fluids.

This treatment has resulted in complications due to the introduction of foreign proteins and transmission of infectious diseases. Further, plasmapheresis has the disadvantage of non-selective removal of all serum proteins, such as VLDL, LDL, and HDL. Moreover, plasmapheresis can result in several side effects including allergic reactions in the form of fever, chills, and rash and possibly even anaphylaxis.

As described above, it is not desirable to remove HDL, which is secreted from both the liver and the intestine as nascent, disk-shaped particles that contain cholesterol and phospholipids. HDL is believed to play a role in reverse cholesterol transport, which is the process by which excess cholesterol is removed from tissues and transported to the liver for reuse or disposal in the bile.

In contrast to plasmapheresis, the LDL-apheresis procedure selectively removes Apo B containing cholesterol, such as LDL, while retaining HDL. Several methods for LDL-apheresis have been developed. These techniques include absorption of LDL in heparin-agarose beads, the use of immobilized LDL-antibodies, cascade filtration absorption to immobilize dextran sulphate, and LDL precipitation at low pH in the presence of heparin. Each method described above is effective in removing LDL. This treatment process has disadvantages, however, including the failure to positively affect HDL or to cause a metabolic shift that can enhance atherosclerosis and other cardiovascular diseases. LDL apheresis merely treats patients with severe hyperlipidemia.

Yet another method of achieving a reduction in plasma cholesterol in homozygous familial hypercholesterolemia, heterozygous familial hypercholesterolemia and patients with acquired hyperlipidemia is an extracorporeal lipid elimination process, referred to as cholesterol apheresis. In cholesterol apheresis, blood is withdrawn from a patient, the plasma is separated from the blood, and the plasma is mixed with a solvent mixture. The solvent mixture extracts lipids from the plasma. Thereafter, the delipidated plasma is recombined with the patient's blood cells and returned to the patient.

Conventional extracorporeal delipidation processes, however, are directed toward the concurrent delipidation of LDL and HDL. This process can have a number of disadvantages. Because LDL is more difficult to delipidate, extracorporeal systems are designed to subject body fluid volumes to substantial processing, possibly through multiple stage solvent exposure and extraction steps. Vigorous multi-stage solvent exposure and extraction can have several drawbacks. It may be difficult to remove a sufficient amount of solvents from the delipidated plasma in order for the delipidated plasma to be safely returned to a patient.

Hence, existing apheresis and extracorporeal systems for treatment of plasma constituents suffer from a number of disadvantages that limit their ability to be used in clinical applications. A need exists for improved systems, apparatuses and methods capable of removing lipids from blood components in order to provide treatments and preventative measures for cardiovascular diseases. What is also needed is a method to selectively remove lipid from HDL particles and thereby create modified HDL particles with increased capacity to accept cholesterol. What is also needed is a method to selectively remove lipid from HDL particles and thereby create modified HDL particles with increased capacity to accept cholesterol, without substantially affecting LDL particles.

SUMMARY OF THE INVENTION

The present invention is directed to systems, apparatus and methods for creating modified HDL particles without substantially affecting LDL. These modified HDL particles are derivatives of HDL with reduced lipid content, particularly reduced cholesterol content. These modified HDL particles have the capacity to bind cholesterol and may be administered to a patient to enhance cellular cholesterol efflux and reduce cholesterol levels in cells, tissues, organs and blood vessels.

The present invention also provides a biological fluid comprising a modified protein distribution wherein the biological fluid had a first state, the first state having alpha high density lipoproteins and pre-beta high density lipoproteins, and wherein the biological fluid has a second state, the second state having an increased concentration of pre-beta high density lipoprotein relative to the first state, after being exposed to a lipid removing agent.

The present invention also provides a biological fluid capable of enhancing an ABCA1 pathway of a patient wherein the biological fluid is made by modifying a fluid having a first concentration of pre-beta high density lipoproteins relative to total protein, wherein the modification increases the concentration of pre-beta high density lipoprotein relative to total protein.

The present invention further provides a method of enhancing an ABCA1 pathway of a patient with a first protein distribution, the first protein distribution having a concentration of pre-beta high density lipoproteins relative to total protein, comprising the step of modifying a fluid containing the first protein distribution by exposing the fluid to a lipid removing agent, wherein the modification increases the concentration of pre-beta high density lipoprotein relative to total protein, and introducing the fluid into the patient.

The present invention further provides a method of modifying a protein distribution in a fluid wherein the protein distribution has a first state, said first state having alpha high density lipoproteins and pre-beta high density lipoproteins, comprising the steps of: exposing said fluid to a lipid removing agent wherein the exposure modifies the protein distribution from the first state into a second state, said second state having an increased concentration of pre-beta high density lipoprotein relative to said first state; and removing said lipid removing agent from the biological fluid.

The present invention discloses a method for removing lipids from fluids, such as blood plasma, and from HDL particles without substantially affecting LDL by treating the fluid with solvents and adding energy to mix the solvents and fluid. Removing lipid from HDL particles creates a modified HDL particle with reduced lipid content, which is capable of binding additional lipid and enhancing cellular cholesterol efflux. More particularly, the present invention is directed toward removal of lipids from HDL particles in blood plasma using either a single solvent or multiple solvents, thereby creating new particles that are derivatives of HDL with reduced lipid content.

In one embodiment of the present invention, LDL and HDL particles are separated prior to treatment of the plasma containing the HDL particles. LDL is extracted and the plasma is treated to reduce the lipid content of HDL particles. Subsequent to LDL removal, the plasma containing HDL particles is exposed to lipid removing agents using the present methods to reduce lipid levels and create particle derivatives of HDL with reduced lipid content. These particles demonstrate enhanced capacity for binding cholesterol. These particle derivatives of HDL and the plasma with reduced lipid content may be administered to the patient in order to enhance cellular cholesterol efflux and treat lipid-associated diseases and conditions.

In another embodiment of the present invention, the LDL is retained (not separated prior to treatment) and a solvent system is employed to selectively remove lipid from HDL and create particles comprised of derivatives of HDL with reduced lipid content while not substantially affecting LDL. The separated plasma is mixed with a solvent system designed to selectively decrease lipid in HDL particles present in the plasma. Care is taken to ensure that the solvent employed, the mixing method employed, procedure, mixing time, and temperature create an optimal solvent system that will selectively remove lipid from HDL, create particles comprised of derivatives of HDL, and leave LDL substantially intact. The at least partially or substantially delipidated plasma, which was separated initially, is then treated appropriately for administration to a patient.

The present invention may be employed to treat plasma obtained from a patient for subsequent administration to the patient or for administration into another patient. The present invention may also be used to treat blood and plasma stored in blood banks in order to create plasma with reduced lipid content and containing particles comprised of derivatives of HDL with reduced lipid content. This treated plasma containing particles comprised of derivatives of HDL with reduced lipid content may be used for heterologous administration to another individual in order to enhance cholesterol efflux in the patient. The present invention may also be employed to create particles comprised of derivatives of HDL that may be collected and stored.

The present method modifies various forms of different HDL particles. Such HDL particles include but are not limited to those HDL particles that have been described based on a variety of methods such as methods that measure charge, density, size and immunoaffinity, including but not limited to electrophoretic mobility, ultracentrifugation, immunoreactivity and other methods known to one of ordinary skill in the art. Such HDL particles include but are not limited to the following: VLDL, a HDL, pre-β HDL (including pre-$β_1$ HDL, pre-$β_2$ HDL and pre-$β_3$ HDL), β HDL, $HDL_2$ (including $HDL_{2a}$ and $HDL_{2b}$), $HDL_3$, VHDL, LpA-I, LpA-II, LpA-I/LpA-II (for a review see Barrans et al., Biochemica Biophysica Acta 1300; 73-85, 1996). Accordingly, practice of the methods of the present invention creates modified HDL particles. These modified HDL particles may be modified in numerous ways, including but not limited to changes in one or more of the following metabolic and or physico-chemical properties: molecular mass (kDa); charge; diameter; shape; density; hydration density; flotation characteristics; content of cholesterol; content of free cholesterol; content of esterified cholesterol; molar ratio of free cholesterol to phospholipids; immunoaffinity; content, activity or helicity of one or more of the following enzymes or proteins (Apo A-1, Apo A-2, Apo D, Apo E, Apo J, Apo A-IV, cholesterol ester transfer protein (CETP), lecithin:cholesterol acyltransferase (LCAT); capacity and/or rate for cholesterol binding, capacity and/or rate for cholesterol transport. The physical-chemical properties of HDL particles are known to one of ordinary skill in the art. For example, pre-β HDL particles have been characterized in terms of their charge, molecular mass (ranging from 40 kDa-420 kDa), size (Stoke's radius 4 nm-15 nm), shape (ellipsoidal, discoidal or spherical) and chemical composition (protein (including Apo A-1), free cholesterol, esterified cholesterol, phospholipids and the ratio of free cholesterol to phospholipids (see Barrans et al., Biochemica Biophysica Acta 1300; 73-85, 1996 for additional details)).

The present invention creates these modified HDL particles without substantially affecting various metabolic and or physico-chemical properties of LDL particles.

In another aspect of the present invention, the modified HDL derivative particles made with the disclosed method are administered to a patient in order to enhance cholesterol efflux from cells. These modified HDL particles may be obtained from the same patient or a different patient who will receive the modified HDL particles. These particles may be combined with plasma treated with the methods of the present invention and containing substantially reduced levels of lipid and then administered to a patient.

The present invention also provides a modified Apo A-1 protein produced by treating plasma with the method of the present invention, wherein the modified Apo A-1 protein has reduced lipid content. The modified Apo A-1 protein is purified and may be administered to a patient either alone or in conjunction with the modified HDL particles with reduced lipid content to enhance cholesterol efflux.

These modified HDL particles may also be combined with heterologous plasma treated with the methods of the present invention and containing substantially reduced levels of lipid and then administered to a patient. These particles may be combined with other plasma constituents, and optionally with red blood cells before administration into the vascular system. Administration of these particles occurs as frequently as necessary to effectuate cholesterol efflux from cells.

The modified HDL particles of the present invention are administered to patients in order to reduce cellular levels of cholesterol, and are indicated for a variety of conditions, including but not limited to atherosclerosis, arteriosclerosis, hyperlipidemia, hypercholesterolemia, obesity, hypertension, stroke, neuroprotection following stroke, inflammation, Alzheimer's disease, diabetes, low endogenous HDL levels, high LDL levels, cardiovascular disease (including atherosclerosis of the coronary arteries, carotid arteries, subelavian, brachial, aorta, iliac, renal, femoral, popliteal, tibial or any other artery in the cardiovascular system), cerebrovascular disease (including atherosclerosis of the internal carotid, middle cerebral, anterior cerebral, posterior cerebral, basilar, cerebellar, and/or spinal arteries, or any branch of these arteries, cerebral cortical end arteries, or any other artery supplying the central nervous system).

The modified HDL particles of the present invention are administered to a patient according to any schedule that is effective to enhance cellular cholesterol efflux. In one non-limiting example, a liter of plasma is treated with the methods of the present invention each week and the treated plasma containing the modified HDL particles is returned to the patient each week for four to six weeks. Alternatively, the modified HDL particles may be separated from the treated plasma and administered in an acceptable vehicle.

It is to be understood that the modified HDL particles of the present invention may be administered in conjunction other regimens and treatments for treatment of the diseases and conditions mentioned above. For example, the modified HDL particles of the present invention may be administered in conjunction with exercise and/or dietary restriction of fat and cholesterol intake.

The modified HDL particles of the present invention may be used in conjunction with administration of agents for reducing cholesterol, reducing LDL levels and enhancing HDL levels. These agents, such as HMG-CoA reductase inhibitors, or statins, may be administered in dosages and according to administration schedules commonly known to one of ordinary skill in the art. Statins include but are not limited to cerivastatin, atorvastatin, fluvastatin, simvastatin, pravastatin and lovastatin. For example, dosages of 10 mg, 20 mg, 40 mg or 80 mg of statins, taken once per day, are commonly employed. Administration of the modified HDL particles of the present invention can eliminate the need for statin therapy in patients or reduce the required dosage of statins.

In another aspect, the modified HDL particles of the present invention are used in conjunction with administration of agents designed to reduce absorption of fat and cholesterol. Such agents, for example ezetimibe, and the clinically appropriate dosages are known to one of ordinary skill in the art.

In yet another aspect of the present invention, the modified HDL particles are used in conjunction with administration of one or more agents such as fibric acid derivatives (gemfibrozil), nicotinic acid (niacin), and bile acid-binding resins (cholestyramine, cholestipol).

In yet another aspect, the modified HDL particles of the present invention are used in conjunction with administration of anti-inflammatory drugs known to one of ordinary skill in the art, such as aspirin. Anti-inflammatory drugs are often prescribed to patients with vascular disease since it is believed that inflammation is a causative factor of atherosclerosis and other vascular diseases.

The modified HDL particles of the present invention are used in conjunction with administration of agents such as statins together with agents designed to reduce absorption of fat and cholesterol. This combination of three therapies is effective in enhancing cholesterol efflux from cells and permits administration of lower dosages of statins. The modified HDL particles of the present invention are also used in conjunction with any of the therapeutic approaches described above.

These modified HDL particles may be stored before use. They may be made from a patient's plasma and returned to that patient. Alternatively, the modified HDL particles may be made from plasma obtained from a first patient and subsequently administered to a second patient. The present invention is useful in creating plasma samples containing modified HDL particles for storage in a plasma bank and subsequent administration to patients.

Accordingly, it is an object of the present invention to provide particles comprising modified HDL particles.

It is another object of the present invention to provide particles comprising modified HDL particles without substantially affecting LDL.

Yet another object of the present invention is to provide particles comprising derivatives of at least one form of HDL, wherein the particle has a reduced cholesterol content.

It is another object of the present invention to provide particles comprising derivatives of at least one form of HDL with a reduced ratio of free cholesterol to phospholipid.

Another object of the present invention is to provide particles comprising derivatives of at least one form of HDL, wherein the particles are pre-β HDL particles.

Yet another object of the present invention is to provide a biological fluid comprising a modified protein distribution wherein the biological fluid had a first state, the first state having alpha high density lipoproteins and pre-beta high density lipoproteins, and wherein the biological fluid has a second state, the second state having an increased concentration of pre-beta high density lipoprotein relative to the first state, after being exposed to a lipid removing agent.

Accordingly, it is an object of the present invention to provide a novel method for creation of particles comprising derivatives of at least one form of HDL.

It is yet another object of the present invention to provide a novel method for creation of particles comprising derivatives of at least one form of HDL without substantially affecting LDL.

Another object of the present invention is to provide a method of modifying a protein distribution in a fluid wherein the protein distribution has a first state, said first state having alpha high density lipoproteins and pre-beta high density lipoproteins, comprising the steps of: exposing said fluid to a lipid removing agent wherein the exposure modifies the protein distribution from the first state into a second state, said second state having an increased concentration of pre-beta high density lipoprotein relative to said first state; and removing said lipid removing agent from the biological fluid.

It is yet another object of the present invention to provide a biological fluid capable of enhancing an ABCA1 pathway of a patient wherein the biological fluid is made by modifying a fluid having a first concentration of pre-beta high density lipoproteins relative to total protein, wherein the modification increases the concentration of pre-beta high density lipoprotein relative to total protein.

Another object of the present invention is to provide a method of enhancing an ABCA1 pathway of a patient with a first protein distribution, the first protein distribution having a concentration of pre-beta high density lipoproteins relative to total protein, comprising the step of modifying a fluid containing the first protein distribution by exposing the fluid to a lipid removing agent, wherein the modification increases the concentration of pre-beta high density lipoprotein relative to total protein, and introducing the fluid into the patient.

Yet another object of the present invention is to provide a novel method for treating diseases associate with lipid accumulation by administering to a patient a composition comprising particles that are derivatives of at least one form of HDL.

It is another object of the present invention to provide a novel method for treating diseases associated with lipid accumulation by administering to a patient a composition comprising particles that are derivatives of at least one form of HDL in conjunction with therapeutic administration of a statin, an inhibitor of cholesterol or lipid uptake, niacin, fibric acid derivatives, bile acid-binding resins, or a combination thereof.

Yet another object of the present invention is to provide a novel method for enhancing cellular cholesterol efflux in a patient comprising administration of a composition comprising particles that are derivatives of at least one form of HDL.

Still another object of the present invention is to provide a novel method for treating atherosclerosis by administering to a patient a composition comprising particles that are derivatives of at least one form of HDL.

Another object of the present invention is to provide a kit useful for treating a biological fluid in order to reduce cholesterol and lipid and to create particles comprising derivatives of at least one form of HDL.

These and other objects, features and advantages of the present invention will become apparent after a review of the following detailed description of the disclosed embodiments and claims.

DETAILED DESCRIPTION OF THE INVENTION

Figure 1:
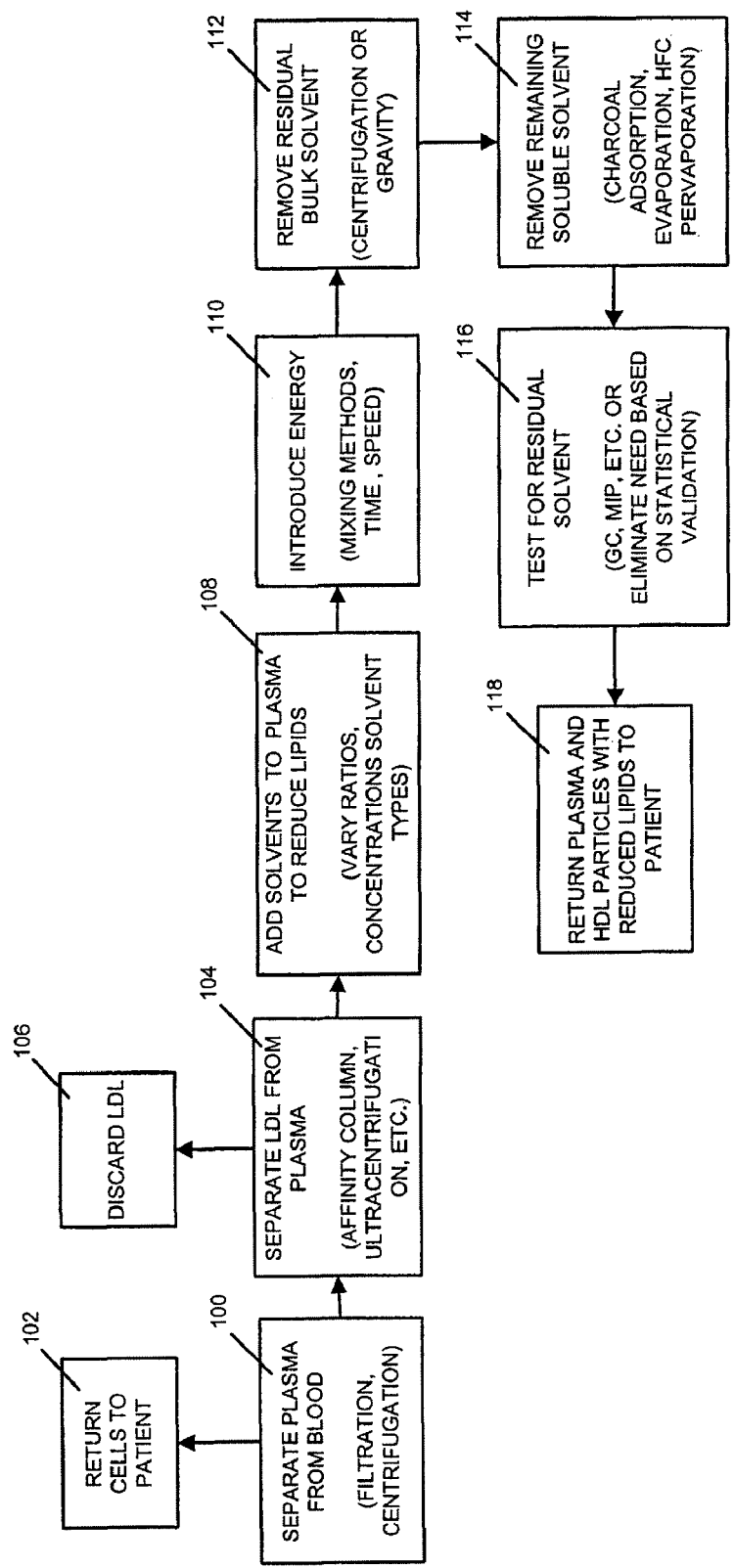
FIG. 1 is a flowchart delineating the steps of the LDL extraction, and subsequent creation of modified HDL particles.

This invention relates to systems, apparatus and methods useful for removing lipid from HDL particles derived primarily from plasma of patients thereby creating modified HDL particles with reduced lipid content, particularly reduced cholesterol content. The present methods create these modified HDL particles with reduced lipid content without substantially modifying LDL particles.

The present invention further provides a biological fluid comprising a modified protein distribution wherein the biological fluid had a first state, the first state having alpha high density lipoproteins and pre-beta high density lipoproteins, and wherein the biological fluid has a second state, the second state having an increased concentration of pre-beta high density lipoprotein relative to the first state, after being exposed to a lipid removing agent. The present invention provides a biological fluid capable of enhancing an ABCA1 pathway of a patient wherein the biological fluid is made by modifying a fluid having a first concentration of pre-beta high density lipoproteins relative to total protein, wherein the modification increases the concentration of pre-beta high density lipoprotein relative to total protein.

The present invention provides newly formed derivatives of HDL particles that may be administered to patients to enhance cellular cholesterol efflux and treat diseases, particularly arteriosclerosis, atherosclerosis, cardiovascular and other lipid-associated diseases.

DEFINITIONS

The term "fluid" is defined as fluids from animals or humans that contain lipids or lipid containing particles, fluids from culturing tissues and cells that contain lipids and fluids mixed with lipid-containing cells. For purposes of this invention, decreasing the amount of lipids in fluids includes decreasing lipids in plasma and particles contained in plasma, including but not limited to HDL particles. Fluids include, but are not limited to: biological fluids; such as blood, plasma, serum, lymphatic fluid, cerebrospinal fluid, peritoneal fluid, pleural fluid, pericardial fluid, various fluids of the reproductive system including, but not limited to, semen, ejaculatory fluids, follicular fluid and amniotic fluid; cell culture reagents such as normal sera, fetal calf serum or serum derived from any animal or human; and immunological reagents, such as various preparations of antibodies and cytokines from culturing tissues and cells, fluids mixed with lipid-containing cells, and fluids containing lipid-containing organisms, such as a saline solution containing lipid-containing organisms. A preferred fluid treated with the methods of the present invention is plasma.

The term "lipid" is defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol.

The term "extraction solvent" is defined as one or more solvents used for extracting lipids from a fluid or from particles within the fluid. This solvent enters the fluid and remains in the fluid until removed by other subsystems. Suitable extraction solvents include solvents that extract or dissolve lipid, including but not limited to phenols, hydrocarbons, amines, ethers, esters, alcohols, halohydrocarbons, halocarbons, and combinations thereof. Preferred extraction solvents are ethers, esters, alcohols, halohydrocarbons, or halocarbons which include, but are not limited to di-isopropyl ether (DIPE), which is also referred to as isopropyl ether, diethyl ether (DEE), which is also referred to as ethyl ether, lower order alcohols such as butanol, especially n-butanol, ethyl acetate, dichloromethane, chloroform, isofluorane, sevoflurane (1,1,1,3,3,3-hexafluoro-2-(fluoromethoxy)propane-d3), perfluorocyclohexanes, trifluoroethane, cyclofluorohexanol, and combinations thereof.

The term "patient" refers to animals and humans, which may be either a fluid source to be treated with the methods of the present invention or a recipient of derivatives of HDL particles and or plasma with reduced lipid content.

The term "HDL particles" encompasses several types of particles defined based on a variety of methods such as those that measure charge, density, size and immunoaffinity, including but not limited to electrophoretic mobility, ultracentrifugation, immunoreactivity and other methods known to one of ordinary skill in the art. Such HDL particles include but are not limited to the following: VLDL, $\alpha$ HDL, pre-$\beta$ HDL (including pre-$\beta_1$ HDL, pre-$\beta_2$ HDL and pre-$\beta_3$ HDL), $\beta$ HDL, $HDL_2$ (including $HDL_{2a}$ and $HDL_{2b}$) $HDL_3$, VHDL, LpA-I, LpA-II, LpA-I/LpA-II (for a review see Barrans et al., Biochemica Biophysica Acta 1300; 73-85, 1996). Accordingly, practice of the methods of the present invention creates modified HDL particles. These modified derivatives of HDL particles may be modified in numerous ways including but not limited to changes in one or more of the following metabolic and or physico-chemical properties (for a review see Barrans et al., Biochemica Biophysica Acta 1300; 73-85, 1996): molecular mass (kDa); charge; diameter; shape; density; hydration density; flotation characteristics; content of cholesterol; content of free cholesterol; content of esterified cholesterol; molar ratio of free cholesterol to phospholipids; immunoaffinity; content, activity or helicity of one or more of the following enzymes or proteins (Apo A-1, Apo A-2, Apo D, Apo E, Apo J, Apo A-IV, cholesterol ester transfer protein (CETP), lecithin:cholesterol acyltransferase (LCAT); capacity and/or rate for cholesterol binding, capacity and/or rate for cholesterol transport.

Methods

The methods of the present invention employ techniques to create HDL particles with reduced lipid content. These HDL particles are obtained from fluids, such as plasma. The first method comprises removal of LDL from plasma before treating the plasma to decrease lipids and to create HDL particles with reduced lipid content. The second method does not remove LDL from plasma before exposure to solvents but employs various solvent systems for enabling selective removal of lipids from HDL particles without substantially affecting LDL. The various steps involved in the two methods are described generally below. Following these general descriptions are descriptions of various embodiments of the methods of the present invention, including variants such as solvents employed, mixing methods, mixing times, and optionally, temperature.

The present invention further provides a method of modifying a protein distribution in a fluid wherein the protein distribution has a first state, said first state having alpha high density lipoproteins and pre-beta high density lipoproteins, comprising the steps of: exposing said fluid to a lipid removing agent wherein the exposure modifies the protein distribution from the first state into a second state, said second state having an increased concentration of pre-beta high density lipoprotein relative to said first state; and removing said lipid removing agent from the biological fluid.

The present invention also provides a method of enhancing an ABCA1 pathway of a patient with a first protein distribution, the first protein distribution having a concentration of pre-beta high density lipoproteins relative to total protein, comprising the step of modifying a fluid containing the first protein distribution by exposing the fluid to a lipid removing agent, wherein the modification increases the concentration of pre-beta high density lipoprotein relative to total protein, and introducing the fluid into the patient.

As discussed above, the methods and systems of the present invention may be composed of numerous configurations. Set forth below are numerous components that may be combined to create the numerous embodiments that are capable of achieving the objectives and advantages described above. These embodiments are described to teach the invention and are not meant to limit the scope of the invention. Rather, each embodiment is but one of many possible configurations that can be used to accomplish the objectives described above.

LDL Extraction and Removal of Lipids from HDL Particles

In one embodiment of the present invention, as shown in FIG. 1, the HDL and LDL particles are separated prior to treatment. FIG. 1 is a flow chart of the process for LDL extraction and removal of lipids from HDL particles.

In step 100 of the process for LDL extraction and removal of lipids from HDL particles, the plasma is separated from the blood. In a preferred embodiment, this is achieved via filtration. In another preferred embodiment, the plasma and blood components are separated via centrifugation. The blood can optionally be combined with an anticoagulant, such as sodium citrate, and centrifuged at forces approximately equal to 2,000 times gravity. The red blood cells are then aspirated from the plasma. In step 102, the cells are returned to the patient. In this particular embodiment of the present invention, the LDL is separated from the plasma in step 104. This is achieved via use of an affinity column, ultracentrifugation, or any other method known to one of ordinary skill in the art. An exemplary method is the use of ultracentrifugation, in which the plasma is passed through the ultracentrifugal separator, thereby parsing out the LDL and HDL particles. The ultracentrifugal separator uses density gradient ultracentrifugation—a sophisticated and highly accurate process that separates lighter portions of lipoprotein from heavier portions by centrifugal force. The LDL is discarded in step 106.

In step 108, solvents are added to the plasma which still contains HDL in order to remove lipids. The solvent types, ratios, and concentrations can vary. The plasma and solvent are introduced into at least one apparatus for mixing, agitating, or otherwise contacting the plasma with the solvent. The plasma may be transported using a continuous or batch process. Furthermore various sensing means may be included to monitor pressures, temperatures, flow rates, solvent levels, and the like (discussed in more detail below).

In step 110, energy is introduced to the system. The various forms of energy employed involve mixing methods, time, and speed (variants of which are discussed in further detail below). Centrifugation is employed in step 112 to remove the residual bulk solvent. The remaining soluble solvent is removed in step 114. This is achieved via charcoal adsorption, evaporation, or HFC pervaporation, as discussed below. In optional step 116, the mixture is tested for residual solvent via gas chromatography (GC) or any other similar means. Optionally, this step is eliminated with statistical validation. In step 118, the plasma with reduced lipid content is returned to the patient. This plasma with at least partially or substantially reduced lipid levels, which was separated initially, is then treated appropriately and subsequently reintroduced into the body.

Selective Removal of Lipid from HDL and Formation of Modified HDL Particles

Figure 2:
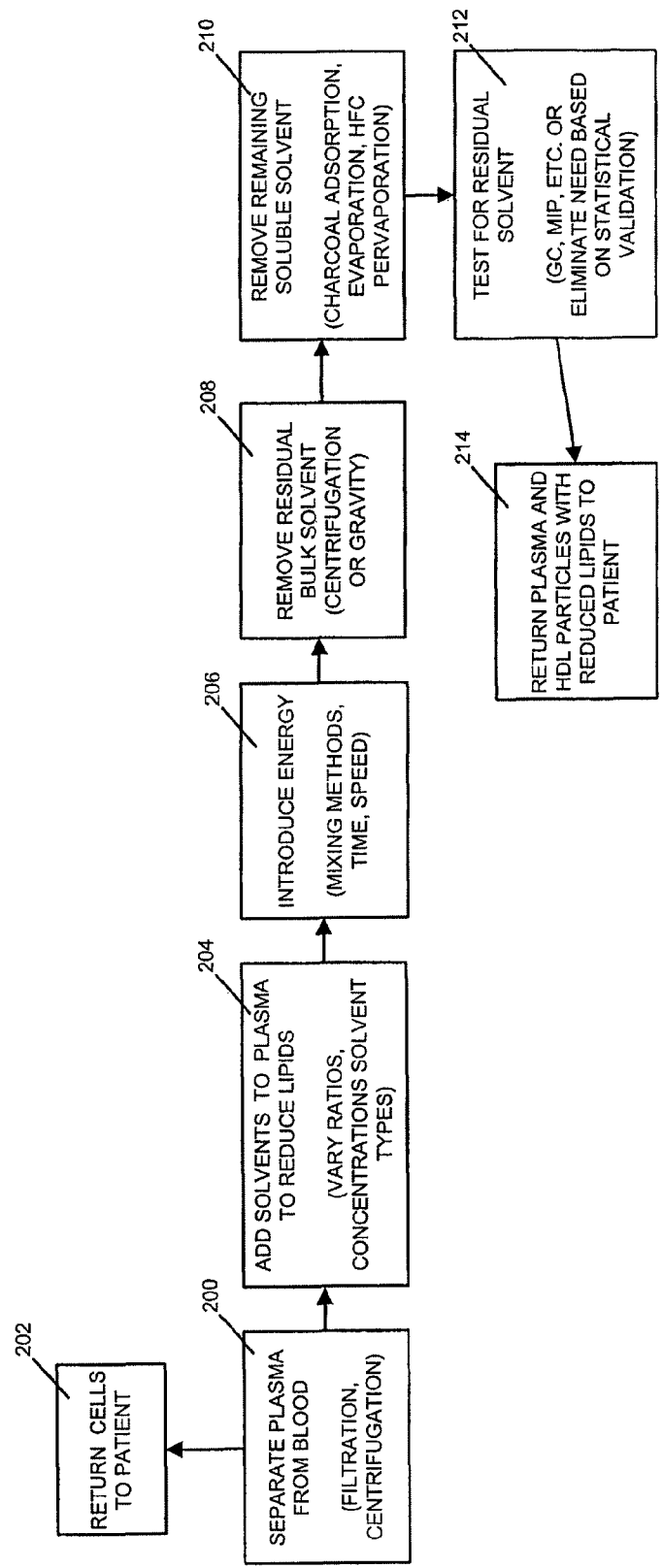
FIG. 2 is a flowchart delineating the steps of the selective creation of modified HDL particles.

FIG. 2 presents a flowchart delineating the steps of the another preferred embodiment of the present invention. In step 200, plasma is separated from the blood via filtration, centrifugation or any other means known to one of ordinary skill in the art. In a preferred embodiment, the blood is passed through a centrifugal separator, which separates the blood into blood cells and plasma. In step 202, the cells are returned to the patient. Solvents are added to the separated plasma in step 204 in order to extract lipids. The solvent system is optimally designed such that only the HDL particles are treated to reduce their lipid levels and LDL remains at least substantially intact. The solvent system includes factoring in variables such as solvent employed, mixing method, time, and temperature. Solvent type, ratios and concentrations may vary in this step. The plasma and solvent are introduced into at least one apparatus for mixing, agitating, or otherwise contacting the plasma with the solvent. The plasma may be transported using a continuous or batch process. Further, various sensing means may be included to monitor pressures, temperatures, flow rates, solvent levels, and the like (discussed in more detail below).

In step 206, energy is introduced into the system in the form of varied mixing methods, time, and speed. Bulk solvents are removed in step 208 via centrifugation. In step 210 the remaining soluble solvent is removed via charcoal adsorption, evaporation, or HFC pervaporation. In step 212, the mixture is optionally tested for residual solvent via use of GC, or similar means. The test for residual solvent may optionally be eliminated based on statistical validation. In step 214, the treated plasma (preferably containing modified HDL particles with reduced lipid content), which was separated initially, is treated appropriately and subsequently returned to the patient.

One of ordinary skill in the art would appreciate that although the processes shown in FIGS. 1 and 2 depict only the main steps of the processes and reference primary elements of the systems, they may optionally contain other elements such as a blood pump for maintaining proper blood volume, a blood pressure meter, a blood anticoagulant agent injecting device, a drip chamber for eliminating air bubbles in the blood, and a heater or cooler for maintaining an appropriate temperature for the blood while it is outside the body.

Variables to be Considered in Employing the Methods of the Present Invention

The present invention employs one of many optimally configured solvent systems designed to remove lipids from HDL particles while not substantially affecting LDL. In the first embodiment, LDL is removed from the plasma before treating the plasma with solvent(s) to create HDL particles with reduced lipid content while retaining the composition of the plasma proteins. In the second embodiment, care is taken to selectively remove lipids from HDL particles without substantially affecting LDL particles. These variables include solvent choice, mixing methods, time, and temperature.

Plasma Separation Procedures

Typical plasma separation procedures are well known to those of ordinary skill in the art and preferably include, but are not limited to, filtration, centrifugation, and aspiration.

LDL Extraction

Methods of LDL extraction are well known to those of ordinary skill in the art. For purposes of the present invention, two preferred methods are, but not limited to, use of an affinity column and ultracentrifugation. The ultracentrifugal separator uses density gradient ultra centrifugation—a sophisticated and highly accurate process that separates lighter portions of lipoprotein from heavier portions by centrifugal force.

Solvents Employed in the Process of Removing Lipids

Numerous organic solvents may be used in the method of this invention for removal of lipid from fluids and HDL particles, provided that the solvents are effective in solubilizing lipids. Suitable solvents comprise mixtures of aromatic, aliphatic, or alicyclic hydrocarbons, ethers, phenols, esters, alcohols, halohydrocarbons, and halocarbons. Preferred solvents are ethers, for example di-isopropyl ether (DIPE). Asymmetrical ethers and halogenated ethers may be used. Particularly preferred, as at least one component, are the $C_4$-$C_8$ containing-ethers, including but not limited to, diethyl ether, and propyl ethers, including but not limited to DIPE. Also useful in the present invention are combinations of ethers, such as DIPE and diethyl ether. Also useful in the present invention are combinations of ethers and alcohols, such as DIPE and butanol. Also preferred in the present invention are combinations of fluoroethers and alcohols, such as sevoflurane and butanol, particularly sevoflurane and n-butanol.

Hydrocarbons in their liquid form dissolve compounds of low polarity such as the lipids in fluids. Accordingly, hydrocarbons comprise any substantially water immiscible hydrocarbon, which is liquid at about 37° C. Suitable hydrocarbons include, but are not limited to the following: $C_5$ to $C_{20}$ aliphatic hydrocarbons such as petroleum ether, hexane, heptane, and octane; haloaliphatic hydrocarbons such as chloroform, 1,1,2-trichloro-1,2,2-trifluoroethane, 1,1,1-trichloroethane, trichloroethylene, tetrachloroethylene, dichloromethane and carbon tetrachloride; thioaliphatic hydrocarbons; perfluorocarbons, such as perfluorocyclohexane, perfluoromethylcyclohexane, and perfluorodimethylcyclohexane; fluoroethers such as sevoflurane; each of which may be linear, branched or cyclic, saturated or unsaturated; aromatic hydrocarbons such as benzene; alkylarenes such as toluene, haloarenes, haloalkylarenes and thioarenes. Other suitable solvents may also include: saturated or unsaturated heterocyclic compounds such as water insoluble derivatives of pyridine and aliphatic, thio or halo derivatives thereof; and perfluorooctyl bromide. Another suitable solvent is perfluorodecalin.

Suitable esters which may be used include, but are not limited to, ethyl acetate, propylacetate, butylacetate and ethylpropionate. Suitable exemplary ketones which may be used include, but are not limited to, methyl ethyl ketone.

Suitable surfactants which may be used, include but are not limited to the following: sulfates, sulfonates, phosphates (including phospholipids), carboxylates, and sulfosuccinates. Some anionic amphiphilic materials useful with the present invention include but are not limited to the following: sodium dodecyl sulfate (SDS), sodium decyl sulfate, bis-(2-ethylhexyl)sodium sulfosuccinate (AOT), cholesterol sulfate and sodium laurate.

The alcohols which are preferred for use in the present invention, when used alone, include those alcohols which are not appreciably miscible with plasma or other biological fluids. When alcohols are used in combination with another solvent, for example, ether, a hydrocarbon, an amine or a combination thereof, $C_1$-$C_8$ containing alcohols may be used. Preferred alcohols for use in combination with another solvent include lower alcohols such as $C_4$-$C_8$ containing alcohols. Accordingly, preferred alcohols that fall within the scope of the present invention are preferably butanols, pentanols, hexanols, heptanols and octanols, and iso forms thereof. Particularly preferred are the butanols (1-butanol and 2-butanol), also referred to as n-butanol. As stated above, the most preferred alcohol is the $C_4$ alcohol, butanol. The specific choice of alcohol will depend on the second solvent employed. In a preferred embodiment, lower alcohols are combined with lower ethers.

Ethers, used alone, or in combination with other solvents, preferably alcohols, are another preferred solvent for use in the method of the present invention. Particularly preferred are the $C_4$-$C_8$ ethers, including but not limited to, ethyl ether, diethyl ether, and propyl ethers, including but not limited to di-isopropyl ether (DIPE). Also useful in the present invention are combinations of ethers, such as di-isopropyl ether and diethyl ether. When ethers and alcohols are used in combination as a first solvent for removing lipid, any combination of alcohol and ether may be used provided the combination is effective to partially or completely remove lipid. When alcohols and ether are combined as a solvent for removing lipid from a fluid, acceptable ratios of alcohol to ether in this solvent are about 0.01 parts to 99.99 parts alcohol to about 99.99 parts to 0.01 parts ether, including a ratio of about 1 part to 25 parts alcohol with about 75 parts to 99 parts ether, a ratio of about 3 parts to 10 parts alcohol with about 90 parts to 97 parts ether, and a preferred ratio of 5 parts alcohol with 95 parts ether. An especially preferred combination of alcohol and ether is the combination of butanol and di-isopropyl ether.

In sum, the particularly preferred solvents include 100 parts di-isopropyl ether, a combination of 95 parts di-isopropyl ether per 5 parts n-butanol, and a combination of 95 parts sevoflurane per 5 parts n-butanol. Acceptable ranges of sevoflurane and n-butanol also include about 0.01 parts to 99.99 parts sevoflurane per about 99.99 parts to 0.01 parts n-butanol, 0.1 parts to 99.9 parts sevoflurane per about 99.9 parts to 0.1 parts n-butanol; 1.0 parts to 99.0 parts sevoflurane per about 99.0 parts to 1.0 parts n-butanol, 10.0 parts to 90.0 parts sevoflurane per about 90.0 parts to 10.0 parts n-butanol, 15.0 parts to 85.0 parts sevoflurane per about 85.0 parts to 15.0 parts n-butanol. Preferred combinations include about 95 parts sevoflurane per about 5.0 parts n-butanol, about 90 parts sevoflurane per about 10 parts n-butanol, about 85 parts sevoflurane per about 15 parts n-butanol, and, more particularly, 97.5 parts sevoflurane per 2.5 parts n-butanol.

Acceptable ratios of solvent to plasma include any combination of solvent and plasma. Most preferred ratios are 2 parts plasma to 1 part solvent, 1 part plasma to 1 part solvent, and 1 part plasma to 2 parts solvent. For example, when using a solvent comprising 95 parts sevoflurane to 5 parts n-butanol, it is preferred to use two parts solvent per one part plasma.

Additionally, when employing a solvent containing n-butanol, the present invention can also use a ratio of solvent to plasma that yields at least 3% n-butanol in the final solvent/plasma mixture. A particularly preferred final concentration of n-butanol in the final solvent/plasma mixture is 3.33%.

Processes to Remove Lipids from Fluids and HDL Particles

The processes employed in the methods of the present invention to reduce lipids in fluids and HDL particles relate directly to energy input. The procedure employed must be designed such that HDL particles are treated to reduce their lipid levels without destruction of plasma proteins or substantially affecting LDL particles. Note that the methods described below may be used to achieve the steps of both of the preferred embodiments of the present invention as described above.

Mixing Methods

The plasma and the solvent are subjected to at least one mixing method for mixing, agitating or otherwise contacting the biological fluid with the solvent. The mixing method employed in the present invention may be one of, but is not limited to, an in-line static mixer, a rotating flask, a vortexer, a centrifuge, a sonicated flask, a high shear tube, a homogenizer, a blender, hollow fiber contactor, a centrifugal pump, a shaker table, a swirling process, a stirring process, an end-over-end rotation of a sealed container, or other suitable devices, or any combination of these devices or processes.

Mixing Duration

The amount of time required for adequate mixing of the solvent with the fluid is related to the mixing method employed. Fluids are mixed for a period of time sufficient to permit intimate contact between the organic and aqueous phases, and for the solvent to at least partially or completely solubilize the lipid. Another consideration is temperature. The balance between the mixing time and temperature must be designed such that it does not encourage the contamination of or deterioration of the blood sample. The time and temperature system is ideally balanced such that the blood sample is still viable and does not deteriorate.

Typically, mixing will occur for a period of about 1 second to about 24 hours, possibly about 1 second to about 2 hours, possibly approximately 1 second to approximately 10 minutes, or possibly about 30 seconds to about 1 hour, depending on the mixing method employed. Non-limiting examples of mixing durations associated with different methods include 1) gentle stirring and end-over-end rotation for a period of about 1 second to about 24 hours, 2) vigorous stirring and vortexing for a period of about 1 second to about 30 minutes, 3) swirling for a period of about 1 second to about 2 hours, or 4) homogenization for a period of about 1 second to about 10 minutes.

Temperature

As described above, temperature is also an important consideration. The temperature is usually set at less that 37° C. so as not to denature the plasma. Optionally, cooler temperatures may also be employed. There are various methods for achieving temperature regulation in this system.

Solvent Extraction Methods

Removal of Residual Bulk Solvent

In a preferred embodiment of the present invention, the residual bulk solvent is removed via centrifugation.

Removal of Remaining Soluble Solvent

Another preferred method of separating solvent is through the use of charcoal, preferably activated charcoal. This charcoal is optionally contained in a column. Alternatively, the charcoal may be in slurry form. Various biocompatible forms of charcoal may be used in these columns.

HFC Pervaporation

Hollow fiber contactors (HFCs) can successfully reduce total concentrations of solvents, such as di-isopropyl ether and di-ethyl ether, in water and plasma, using different HFCs, pressures, and flow rates. HFCs may have a total surface area of permeable membrane formed by the hollow fibers between about 4,200 square centimeters and about 18,000 square centimeters, depending on the type of HFC used. Further, the gas flow rate was varied in these experiments from between about 2 liters per minute to about 10 liters per minute, and the plasma flow rate was varied from between about 10 mL per minute to about 60 mL per minute. Operation in this manner can reduce the initial concentrations of solvents from between about 28,000 parts per million (ppm) and 9,000 ppm to between about 1327 ppm and about 0.99 ppm within between about 14 minutes and 30 minutes.

In one embodiment of the solvent removal system of the present invention, the solvent-treated plasma containing residual soluble solvent is typically first introduced into a circulation loop including, for instance, a recirculating vessel, a fluid transport means such as tubing, valves, a pump, and a solvent extracting device, such as a HFC. In this circulation loop, the HFC functions as a recirculating, solvent-extraction device. The plasma/solvent is circulated through the hollow fiber of the HFC, thereby contacting the extraction solvent with a gas or a second extraction solvent, circulating through the shell of the HFC. If a volatile solvent is used as the first extraction solvent, any gas capable of extracting the first extraction solvent from the delipidated plasma may be used, including, but not limited to, nitrogen and air.

SPECIFIC EMBODIMENTS OF THE PRESENT INVENTION

The above-described components can be integrated into a plurality of different embodiments to enable the practice of the present invention. Certain specific embodiments shall be described herein to particularly highlight defined approaches to practicing the present invention. The embodiments listed below do not represent every variation of the present invention and are designed to exemplify the present invention and, in certain cases, represent preferred approaches to practicing the present invention.

Figure 19:
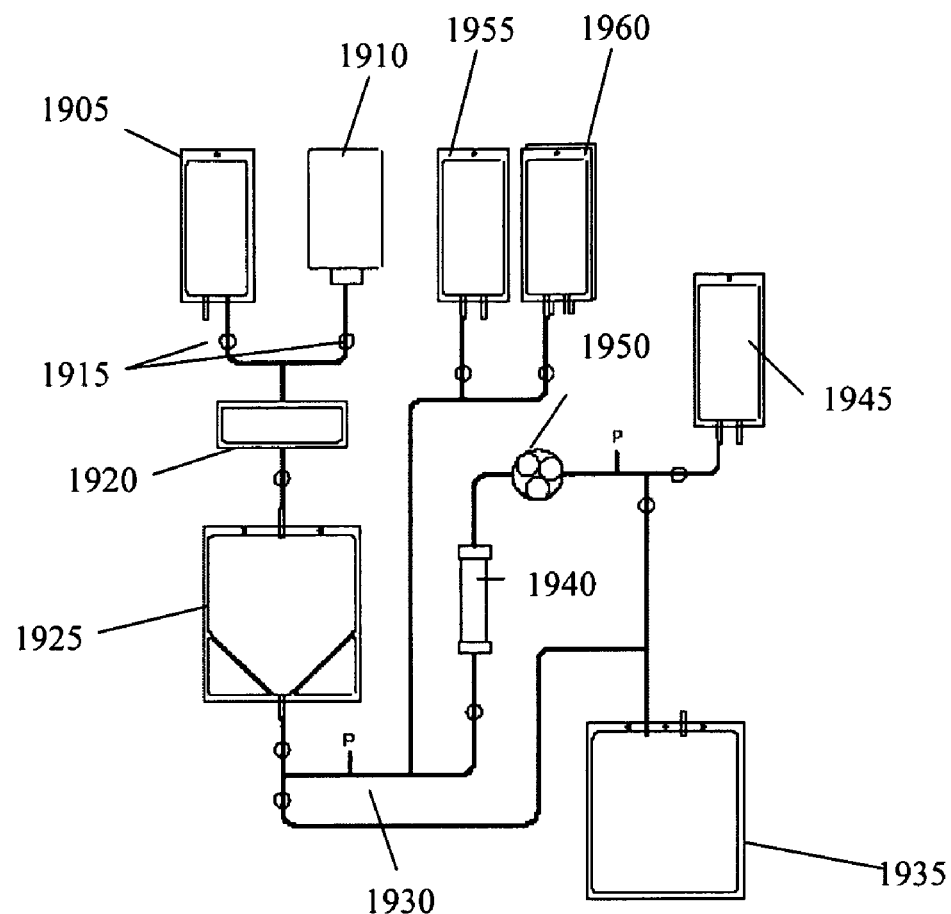
FIG. 19 is a schematic representation of a plurality of components used in the present invention to achieve the novel delipidation processes disclosed herein.
Figure 20:
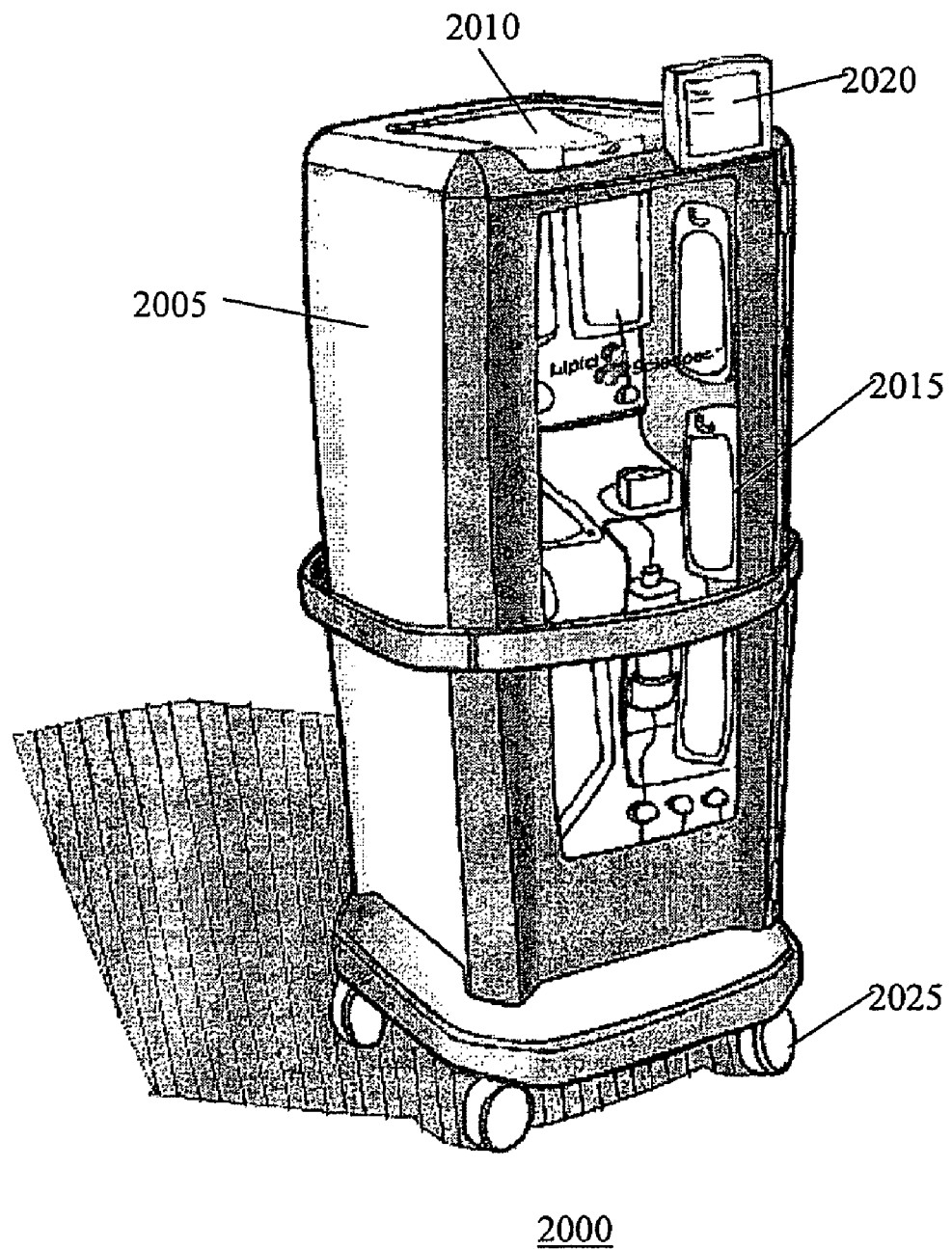
FIG. 20 is one embodiment of a configuration of a plurality of components used in the present invention to achieve the novel delipidation processes disclosed herein.
Figure 21:
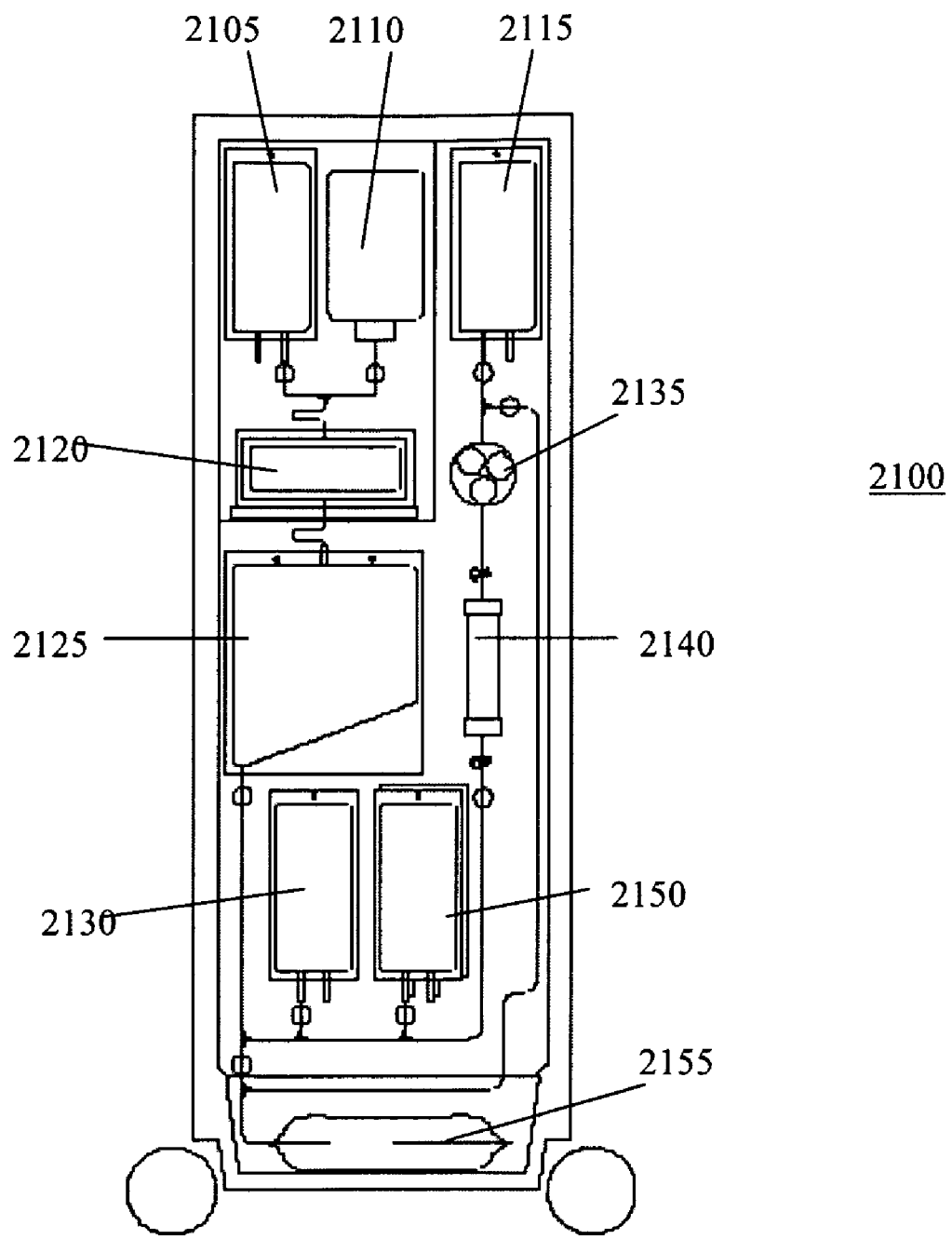
FIG. 21 is another embodiment of a configuration of a plurality of components used in the present invention to achieve the novel delipidation processes disclosed herein.

Referring to FIGS. 19 through 21, a plurality of embodiments depicting different systems capable of practicing the present invention are shown. It should be understood that each embodiment has different advantages and disadvantages, from a cost and usage perspective, and that none of the embodiments are specifically preferred relative to other embodiments. FIG. 19 depicts a basic component flow diagram defining elements of the HDL modification system 1900. A fluid input is provided 1905 and connected via tubing to a mixing device 1920. A solvent input is provided 1910 and also connected via tubing to a mixing device 1920. Preferably valves 1915 are used to control the flow of fluid from fluid input 1905 and solvent from solvent input 1910. It should be appreciated that the fluid input 1905 preferably contains any fluid that includes HDL particles, including plasma having LDL particles or devoid of LDL particles, as discussed above. It should further be appreciated that solvent input 1910 can include a single solvent, a mixture of solvents, or a plurality of different solvents that are mixed at the point of solvent input 1910. While depicted as a single solvent container, solvent input 1910 can comprise a plurality of separate solvent containers. The types of solvents that are used and preferred are discussed above.

The mixer 1920 mixes fluid from fluid input 1905 and solvent from solvent input 1910 to yield a fluid-solvent mixture. Preferably, mixer 1920 is capable of using a shaker bag mixing method with the input fluid and input solvent in a plurality of batches, such as 1, 2, 3 or more batches. An exemplary mixer is a Barnstead Labline orbital shaker table. Once formed, the fluid-solvent mixture is directed, through tubing and controlled by at least one valve, to a separator 1925. In a preferred embodiment, separator 1925 is capable of performing bulk solvent separation through gravity separation in a funnel-shaped bag.

In the separator 1925, the fluid-solvent mixture separates into a first layer and second layer. The first layer comprises a mixture of solvent and lipid that has been removed from the HDL particles. The second layer comprises a mixture of residual solvent, modified HDL particles, and other elements of the input fluid. One of ordinary skill in the art would appreciate that the composition of the first layer and the second layer would differ based upon the nature of the input fluid. Once the first and second layers separate in separator 1925, the second layer is transported through tubing to a solvent extraction device 1940. Preferably, a pressure sensor 1930 and valve is positioned in the flow stream to control the flow of the second layer to the solvent extraction device 1940.

The opening and closing of valves to enable the flow of fluid from input containers 1905, 1910 is preferably timed using mass balance calculations derived from weight determinations of the fluid inputs 1905, 1910 and separator 1925. For example, the valves between separator 1925 and waste container 1935 and between separator 1925 and solvent extraction device 1940 open after the input masses (fluid and solvent) substantially balances with the mass in separator 1925 and a sufficient period of time has elapsed to permit separation between the first and second layers, as discussed above. Depending on what solvent is used, and therefore which layer settles to the bottom of the separator 1925, either the valve between separator 1925 and waste container 1935 is opened or between separators 1925 and solvent extraction device 1940 is opened. One of ordinary skill in the art would appreciate that the timing of the opening is dependent upon how much fluid is in the first and second layers and would further appreciate that it is preferred to keep the valve between separator 1925 and waste container 1935 open just long enough to remove all of the first layer and some of the second layer, thereby ensuring that as much solvent as possible has been removed from the fluid being sent to the solvent extraction device 1940.

Preferably, a glucose input 1955 and saline input 1960 is in fluid communication with the fluid path leading from the separator 1925 to the solvent extraction device 1940. A plurality of valves is also preferably incorporated in the flow stream from the glucose input 1955 and saline input 1960 to the tubing providing the flow path from the separator 1925 to the solvent extraction device 1940. Glucose and saline are incorporated into the present invention in order to prime the solvent extraction device 1940 prior to operation of the system. Where such priming is not required, the glucose and saline inputs are not required. Also, one of ordinary skill in the art would appreciate that the glucose and saline inputs can be replaced with other primers if the solvent extraction device 1940 requires it.

The solvent extraction device 1940 is preferably a charcoal column designed to remove the specific solvent used in the solvent input 1910. An exemplary solvent extraction device 1940 is an Asahi Hemosorber charcoal column. A pump 1950 is used to move the second layer from the separator 1925, through the solvent extraction device 1940, and to an output container 1945. The pump is preferably a peristaltic pump, such as a Masterflex Model 77201-62.

The first layer is directed to a waste container 1935 that is in fluid communication with separator 1925 through tubing and at least one valve. Additionally, other waste, if generated, can be directed from the fluid path connecting solvent extraction device 1940 and output container 1945 to waste container 1935.

Preferably, an embodiment of the present invention uses gravity, wherever practical, to move fluid through each of the plurality of components. For example, preferably gravity is used to drain the input plasma 1905 and input solvent 1910 into the mixer 1920. Where the mixer 1920 comprises a shaker bag and separator 1925 comprises a funnel bag, fluid is moved from the shaker bag to the funnel bag and, subsequently, to the waste container 1935, if appropriate, using gravity.

In an additional step, not shown in FIG. 19, the output fluid in output container 1945 would be subjected to a solvent detection system, or lipid removing agent detection system, to determine if any solvent, or other undesirable component, is in the output fluid. In one embodiment, the output fluid is subjected to sensors that are capable of determining the concentrations of solvents introduced in the solvent input, such as n-butanol or di-isopropyl ether. This is an important measurement because the output fluid is returned to the bloodstream of the patient and the solvent concentrations must be below a predetermined level to carry out this operation safely. The sensors are preferably capable of providing such concentration information on a real-time basis and without having to physically transport a sample of the output fluid, or air in the headspace, to a remote device.

In one embodiment, molecularly imprinted polymer technology is used to enable surface acoustic wave sensors. A surface acoustic wave sensor receives an input, through some interaction of its surface with the surrounding environment, and yields an electrical response, generated by the piezoelectric properties of the sensor substrate. To enable the interaction, molecularly imprinted polymer technology is used. Molecularly imprinted polymers are plastics programmed to recognize target molecules, like pharmaceuticals, toxins or environmental pollutants, in complex biological samples. The molecular imprinting technology is enabled by the polymerization of one or more functional monomers with an excess of a crosslinking monomer in presence of a target template molecule exhibiting a structure similar to the target molecule that is to be recognized, i.e. the target solvent.

The use of molecularly imprinted polymer technology to enable surface acoustic wave sensors is preferred relative to other technological approaches because they can be made more specific to the concentrations of targeted solvents and are capable of differentiating such targeted solvents from other possible interferents. As a result, the presence of acceptable interferents that may have similar structures and/or properties to the targeted solvents would not prevent the sensor from accurately reporting existing respective solvent concentrations.

Alternatively, if the input solvent comprises certain solvents, such as n-butanol, electrochemical oxidation could be used to measure the solvent concentration. Electrochemical measurements have several advantages. They are simple, sensitive, fast, and have a wide dynamic range. The instrumentation is simple and not affected by humidity. In one embodiment, the target solvent, such as n-butanol, is oxidized on a platinum electrode using cyclic voltammetry. This technique is based on varying the applied potential at a working electrode in both the forward and reverse directions, at a predefined scan rate, while monitoring the current. One full cycle, a partial cycle, or a series of cycles can be performed. While platinum is the preferred electrode material, other electrodes, such as gold, silver, iridium, or graphite, could be used. Although, cyclic voltammetric techniques are used, other pulse techniques such as differential pulse voltammetry or square wave voltammetry may increase the speed and sensitivity of measurements. The alternative, a Taguchi sensor, is not preferred because it does not effectively operate in humid conditions.

The present invention expressly covers any and all forms of automatically sampling and measuring, detecting, and analyzing an output fluid, or the headspace above the output fluid. For example, such automated detection can be achieved by integrating a mini-gas chromatography (GC) measuring device that automatically samples air in the output container, transmits it to a GC device optimized for the specific solvents used in the delipidation process, and, using known GC techniques, analyzes the sample for the presence of the solvents.

Referring back to FIG. 19, suitable materials for use in any of the apparatus components as described herein include materials that are biocompatible, approved for medical applications that involve contact with internal body fluids, and in compliance with U.S. PVI or ISO 10993 standards. Further, the materials should not substantially degrade from, for instance, exposure to the solvents used in the present invention, during at least a single use. The materials should typically be sterilizable either by radiation or ethylene oxide (EtO) sterilization. Such suitable materials should be capable of being formed into objects using conventional processes, such as, but not limited to, extrusion, injection molding and others. Materials meeting these requirements include, but are not limited to, nylon, polypropylene, polycarbonate, acrylic, polysulphone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA), which is available as TEFLON PFA from E.I. du Pont de Nemours and Company, and combinations thereof.

The valves used in each embodiment may be composed of, but are not limited to, pinch, globe, ball, gate or other conventional valves. Preferably, the valves are occlusion valves such as Acro Associates' Model 955 valve. However, the invention is not limited to a valve having a particular style. Further, the components of each system described below may be physically coupled together or coupled together using conduits that may be composed of flexible or rigid pipe, tubing or other such devices known to those of ordinary skill in the art.

Referring to FIG. 20, a specific configuration 2000 of the present invention is shown. A preferred configuration 2000 comprises an enclosed housing 2005 capable of safely containing volatile fluids, such as solvents. In a preferred embodiment, the enclosed housing 2005 comprises a door 2015 with a clear door to observe the delipidation process in operation, a mobile base 2025, a control display 2020, a clear top 2010, and a filter and air circulating system [not shown]. The interface screen of the control display 2020 is preferably functional when the door 2015 is open to enable system set up and priming a solvent extraction device but does not permit the system to delipidate an input fluid until the door 2015 is closed and, preferably, locked. It is also preferred to have a waste or overflow tray capable of trapping any fluid leaks, overflows, or other spills at the base of the enclosed housing 2005 in a manner that permits the tray to be readily removed without opening the housing 2005.

Referring to FIG. 21, a configuration of basic components of the HDL modification system 2100 is shown. A fluid input is provided 2105 and connected via tubing to a mixing device 2120. A solvent input is provided 2110 and also connected via tubing to a mixing device 2120. Preferably valves are used to control the flow of fluid from fluid input 2105 and solvent from solvent input 2110. It should be appreciated that the fluid input 2105 preferably contains any fluid that includes HDL particles, including plasma having LDL particles or devoid of LDL particles, as discussed above. It should further be appreciated that solvent input 2110 can include a single solvent, a mixture of solvents, or a plurality of different solvents that are mixed at the point of solvent input 2110. While depicted as a single solvent container, solvent input 2110 can comprise a plurality of separate solvent containers. The types of solvents that are used and preferred are discussed above.

The mixer 2120 mixes fluid from fluid input 2105 and solvent from solvent input 2110 to yield a fluid-solvent mixture. Preferably, mixer 2120 is capable of using a shaker bag mixing method with the input fluid and input solvent in a plurality of batches, such as 1, 2, 3 or more batches. Once formed, the fluid-solvent mixture is directed, through tubing and controlled by at least one valve, to a separator 2125. In a preferred embodiment, separator 2125 is capable of performing bulk solvent separation through gravity separation in a funnel-shaped bag.

In the separator 2125, the fluid-solvent mixture separates into a first layer and second layer. The first layer comprises a mixture of solvent and lipid that has been removed from the HDL particles. The second layer comprises a mixture of residual solvent, modified HDL particles, and other elements of the input fluid. One of ordinary skill in the art would appreciate that the composition of the first layer and the second layer would differ based upon the nature of the input fluid. Once the first and second layers separate in separator 2125, the second layer is transported through tubing to a solvent extraction device 2140. Preferably, a pressure sensor and valve is positioned in the flow stream to control the flow of the second layer to the solvent extraction device 2140.

Preferably, a glucose input 2130 and saline input 2150 is in fluid communication with the fluid path leading from the separator 2125 to the solvent extraction device 2140. A plurality of valves is also preferably incorporated in the flow stream from the glucose input 2130 and saline input 2150 to the tubing providing the flow path from the separator 2125 to the solvent extraction device 2140. Glucose and saline are incorporated into the present invention in order to prime the solvent extraction device 2140 prior to operation of the system. Where such priming is not required, the glucose and saline inputs are not required. Also, one of ordinary skill in the art would appreciate that the glucose and saline inputs can be replaced with other primers if the solvent extraction device 2140 requires it.

The solvent extraction device 2140 is preferably a charcoal column designed to remove the specific solvent used in the solvent input 2110. An exemplary solvent extraction device 2140 is an Asahi Hemosorber charcoal column. A pump 2135 is used to move the second layer from the separator 2125, through the solvent extraction device 2140, and to an output container 2115. The pump is preferably a peristaltic pump, such as a Masterflex Model 77201-62.

The first layer is directed to a waste container 2155 that is in fluid communication with separator 2125 through tubing and at least one valve. Additionally, other waste, if generated, can be directed from the fluid path connecting solvent extraction device 2140 and output container 2115 to waste container 2155.

Preferably, an embodiment of the present invention uses gravity, wherever practical, to move fluid through each of the plurality of components. For example, preferably gravity is used to drain the input plasma 2105 and input solvent 2110 into the mixer 2120. Where the mixer 2120 comprises a shaker bag and separator 2125 comprises a funnel bag, fluid is moved from the shaker bag to the funnel bag and, subsequently, to the waste container 2155, if appropriate, using gravity.

In general, the present invention preferably comprises configurations wherein all inputs, such as input plasma and input solvents, disposable elements, such as mixing bags, separator bags, waste bags, solvent extraction devices, and solvent detection devices, and output containers are in easily accessible positions and can be readily removed and replaced by a technician.

To enable the operation of the above described embodiments of the present invention, it is preferable to supply a user of such embodiments with a packaged set of components, in kit form, comprising each component required to practice the present invention. Such a kit would preferably include an input fluid container (i.e. a high density lipoprotein source container), a lipid removing agent source container (i.e. a solvent container), disposable components of a mixer, such as a bag or other container, disposable components of a separator, such as a bag or other container, disposable components of a solvent extraction device (i.e. a charcoal column), an output container, disposable components of a waste container, such as a bag or other container, solvent detection devices, and, a plurality of tubing and a plurality of valves for controlling the flow of input fluid (high density lipoprotein) from the input container and lipid removing agent (solvent) from the solvent container to the mixer, for controlling the flow of the mixture of lipid removing agent, lipid, and particle derivative to the separator, for controlling the flow of lipid and lipid removing agent to a waste container, for controlling the flow of residual lipid removing agent, residual lipid, and particle derivative to the extraction device, and for controlling the flow of particle derivative to the output container.

In one embodiment, a kit comprises a plastic container having disposable components of a mixer, such as a bag or other container, disposable components of a separator, such as a bag or other container, disposable components of a waste container, such as a bag or other container, and, a plurality of tubing and a plurality of valves for controlling the flow of input fluid (high density lipoprotein) from the input container and lipid removing agent (solvent) from the solvent container to the mixer, for controlling the flow of the mixture of lipid removing agent, lipid, and particle derivative to the separator, for controlling the flow of lipid and lipid removing agent to a waste container, for controlling the flow of residual lipid removing agent, residual lipid, and particle derivative to the extraction device, and for controlling the flow of particle derivative to the output container. Disposable components of a solvent extraction device (i.e. a charcoal column), the input fluid, the input solvent, and solvent extraction devices are provided separately.

Administration Schedule

The modified HDL particles of the present invention may be administered according to any schedule that is effective in promoting cellular cholesterol efflux.

In one embodiment, blood is withdrawn from a patient in a volume sufficient to produce about 1 liter of plasma. The blood is separated into plasma and red blood cells using methods commonly known to one of skill in the art, such as plasmapheresis, and the red blood cells are stored in an appropriate storage solution or returned to the patient during plasmapheresis. The red blood cells are preferably returned to the patient during plasmapheresis. Physiological saline is also optionally administered to the patient to replenish volume. The 1 liter of plasma is treated with any of the methods of the present invention to create HDL particles with reduced lipid content while not substantially affecting LDL. The resulting treated plasma containing the HDL particles with reduced lipid and substantially unaffected LDL content is optionally combined with the patient's red blood cells, if the red cells were not already returned during plasmapheresis, and administered to the patient. One route of administration is through the vascular system, preferably intravenously. This treatment regimen is repeated weekly for about 5 to 6 weeks. Enhanced cholesterol efflux is observed in the patient after the treatment.

In another embodiment, blood is withdrawn from a patient in a volume sufficient to produce about 1 liter of plasma. The blood is separated into plasma and red blood cells using methods commonly known to one of skill in the art, such as plasmapheresis, and the red blood cells are stored in an appropriate storage solution or returned to the patient during plasmapheresis. The 1 liter of plasma is treated to remove the LDL component before further treatment of the plasma. The 1 liter of plasma is treated with the method of the present invention to create HDL particles with reduced lipid content. The resulting treated plasma containing the HDL particles with reduced lipid is optionally combined with the patient's red blood cells, if the red cells were not already returned during plasmapheresis, and administered to the patient. One route of administration is through the vascular system, preferably intravenously. This treatment regimen is repeated weekly for about 5 to 6 weeks.

It is to be understood that other volumes of plasma may be treated with the method of the present invention, and administered to a patient on various administration schedules. For a batch process, volumes of 100 ml to 3500 ml of plasma may be treated with the present method. The frequency of treatment may also vary from between several times per week to once a month or less, depending on the volume to be treated and the severity of the condition of the patient.

In another approach of the present invention, following removal of a desired volume of a patient's blood, separation of the blood into plasma and red blood cells and treatment of the plasma to reduce lipid levels, the HDL particles with reduced lipid content are isolated from the plasma and administered to the patient in an acceptable vehicle.

In yet another embodiment, heterologous plasma may be obtained, treated with the method of the present invention and the treated plasma containing HDL particles with reduced lipid content administered to a patient who was not the source of the plasma. In a further embodiment, heterologous plasma may be obtained, treated with the method of the present invention and the HDL particles with reduced lipid content are separated from the treated plasma. These HDL particles with reduced lipid content may be administered in an acceptable vehicle to a patient who was not the source of the plasma.

In still another embodiment, following removal of a desired volume of a patient's blood, the patient is permitted to recover for 1 to 4 days in terms of producing new blood and attaining endogenous plasma HDL levels substantially similar to plasma HDL levels before removing the blood. The removed blood is separated into plasma and red blood cells and the plasma is treated to reduce lipid levels. The HDL particles with reduced lipid content are isolated from the plasma and administered to the patient. Alternatively, the HDL particles with reduced lipid content are not isolated from the plasma and the treated plasma is administered to the patient.

In another embodiment plasma is treated with the methods of the present invention to reduce lipid levels. Next, Apo A-1 protein is purified from this treated plasma using techniques such as affinity chromatography. The resulting purified, modified Apo A-1 protein is administered in an acceptable vehicle to a patient together with the modified HDL particles with reduced lipid content. These modified HDL particles with reduced lipid content may be provided to the patient as isolated HDL particles in an acceptable vehicle or included with the treated plasma.

Administration with Other Therapies

The modified HDL particles of the present invention may be administered in conjunction with one or more additional therapeutic approaches. The modified HDL particles of the present invention may be administered in conjunction with exercise and dietary restriction of fat and cholesterol intake.

The modified HDL particles of the present invention may be administered in conjunction with administration of agents for reducing cholesterol, reducing LDL levels and enhancing HDL levels. These agents, such as HMG-CoA reductase inhibitors, or statins, may be administered in dosages and according to administration schedules commonly known to one of ordinary skill in the art. Statins include but are not limited to cerivastatin, atorvastatin, fluvastatin, simvastatin, pravastatin and lovastatin. For example, dosages of 10 mg, 20 mg, 40 mg or 80 mg of statins, taken once per day, are commonly employed. Administration of the modified HDL particles of the present invention can eliminate the need for statin therapy in patients or reduce the required dosage of statins.

In another aspect, the modified HDL particles of the present invention are used in conjunction with administration of agents designed to reduce absorption of fat and cholesterol. Such agents, for example ezetimibe, and the clinically appropriate dosages are known to one of ordinary skill in the art.

In yet another aspect, the modified HDL particles of the present invention are used in conjunction with administration of one or more agents such as fibric acid derivatives (gemfibrozil), nicotinic acid (niacin), and bile acid-binding resins (cholestyramine, cholestipol), and the clinically appropriate dosages are known to one of ordinary skill in the art.

In yet another aspect, the modified HDL particles of the present invention are used in conjunction with administration of anti-inflammatory drugs, such as aspirin, known to one of ordinary skill in the art. The clinically appropriate dosages of anti-inflammatory drugs are known to one of ordinary skill in the art. Anti-inflammatory drugs are often prescribed to patients with vascular disease since it is believed that inflammation is a causative factor of atherosclerosis and other vascular diseases.

The modified HDL particles of the present invention are used in conjunction with administration of agents such as statins and with agents designed to reduce absorption of fat and cholesterol. This combination of three therapies is effective in enhancing cholesterol efflux from cells and permits administration of lower dosages of statins. The modified HDL particles of the present invention are also used in conjunction with any of the therapeutic approaches described above.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Separation and Characterization of Total Cholesterol, Apolipoprotein A1 (Apo A-1), Apolipoprotein B (Apo B) and Phospholipids in Normal Plasma A 25 ml pool of plasma was characterized in terms of total cholesterol, apolipoprotein A1 (Apo A-1), apolipoprotein B (Apo B) and phospholipids. An aliquot of 1 ml of the pooled plasma was loaded onto a Sephacryl S-300 26/60 (FPLC) column. An elution buffer of phosphate buffered saline containing 1 mM EDTA was applied to the column and eluted at 2 ml/min. About 96 fractions were collected, one every 43 seconds beginning 41 minutes after application of the plasma sample. Each fraction was characterized in terms of total cholesterol, Apo A-1, Apo B and phospholipids.

Figure 3:
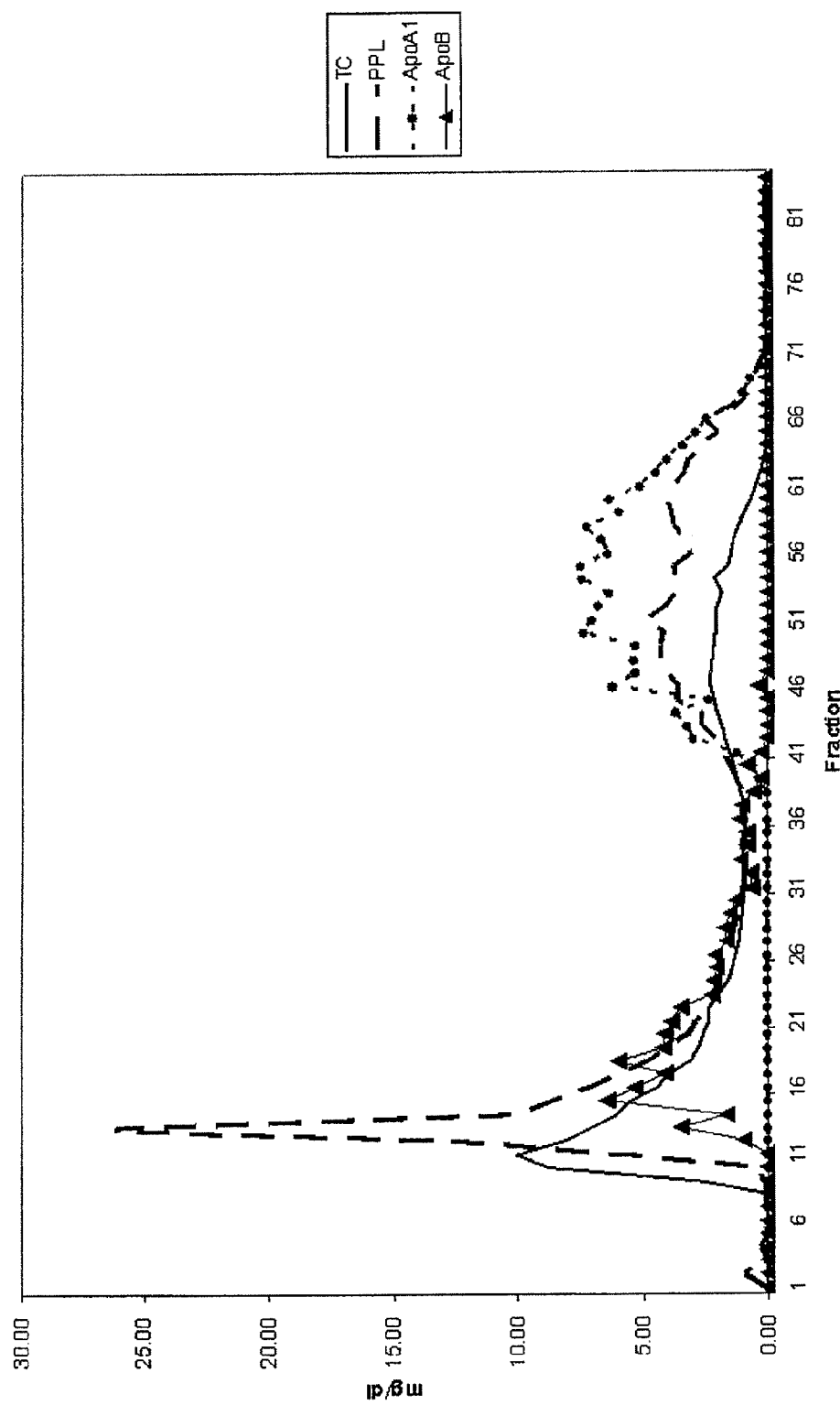
FIG. 3 is a schematic of an FPLC profile of a sample of plasma from a pool of normal plasma. Total cholesterol (TC) is represented as a continuous line; phospholipid (PPL) is the dashed line; apolipoprotein A1 (Apo A-1) is the dashed line with a symbol; and, apolipoprotein B (Apo B) is represented by the line with a triangle. Shown are the amounts of these compounds (mg/dl) in each FPLC fraction.

Apo B containing particles comprised of very low density lipoprotein (VLDL), intermediate density lipoprotein (IDL) and low density lipoprotein (LDL) particles eluted in fractions 10-40. Apo A-1 containing particles comprised of high density lipoprotein (HDL) particles eluted in the remaining fractions. The results are displayed in FIG. 3. An analysis of total plasma cholesterol indicated a clear separation of the LDL particles from the HDL particles. The distribution of Apo A-1 and Apo B in the corresponding fractions confirmed the separation of these particles.

EXAMPLE 2

Selective Creation of Apo A-1-Associated HDL Particles with Reduced Cholesterol or with Reduced Cholesterol and Phospholipids Using DIPE This selective plasma treatment method employs a ratio of 1:1 DIPE:plasma. The sample was vortexed for 15 seconds and then permitted to separate by gravity. Activated charcoal was used to remove residual DIPE after the process and several different hematological parameters were measured.

The delipidated sample was then applied to a column and treated as explained in Example 1. This method removed about 10% of total cholesterol, 12% of Apo B, 17% of Apo A-1 and about 11% of phospholipids.

Figure 4:
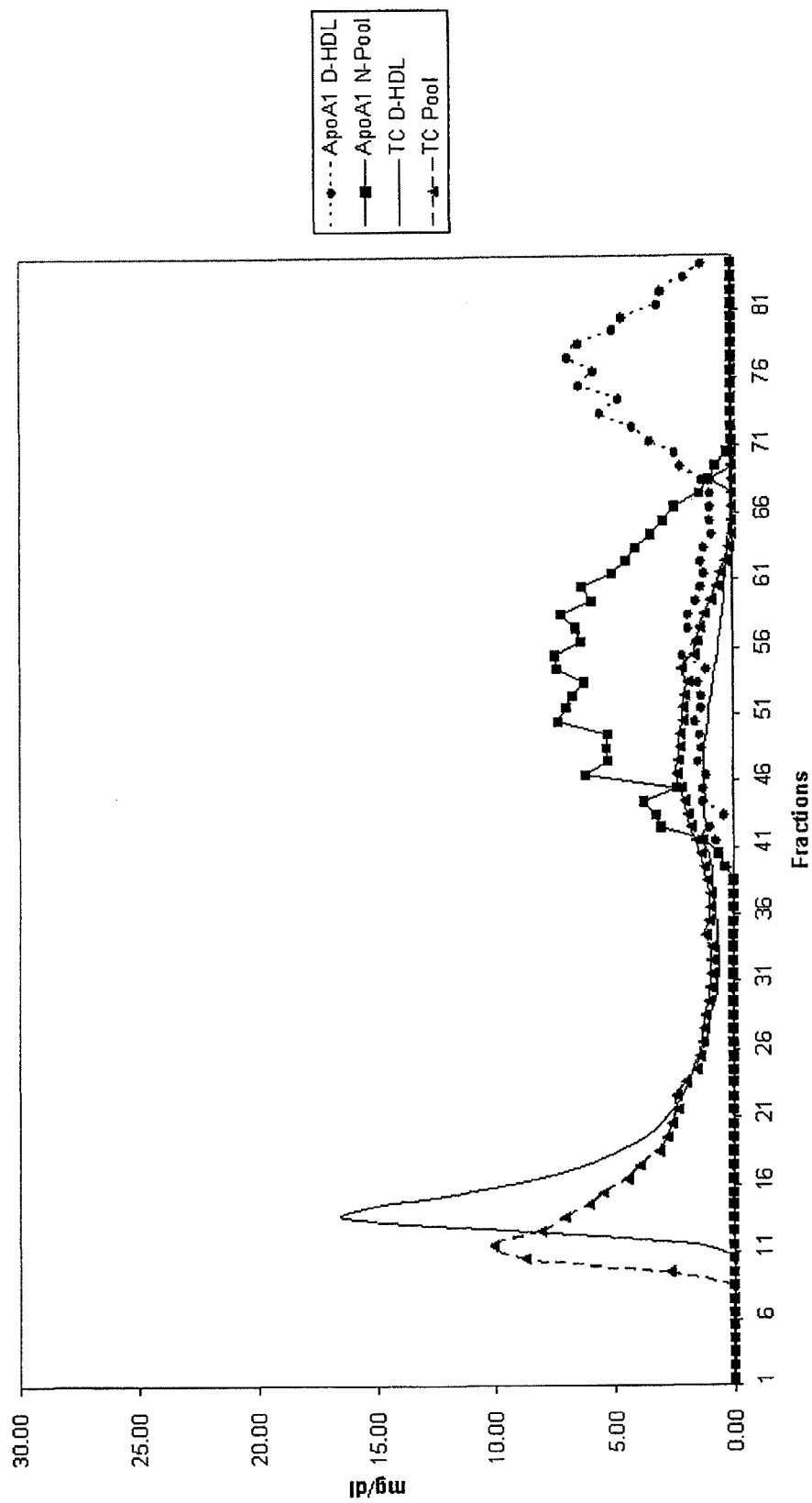
FIG. 4 is a schematic of an FPLC profile of an aliquot from the pool of normal plasma which was subjected to a solvent of 100% diisopropyl ether (DIPE) to remove lipid from HDL. Total cholesterol (TC) in the normal sample from FIG. 3 is represented here as a dashed line with triangles. TC in the normal plasma subjected to DIPE is shown as a solid line. Apo A-1 in the normal sample from FIG. 3 is represented here as a solid line with square symbols. Apo A-1 in the normal plasma subjected to DIPE is shown as a dashed line with a dot symbol.
Figure 5:
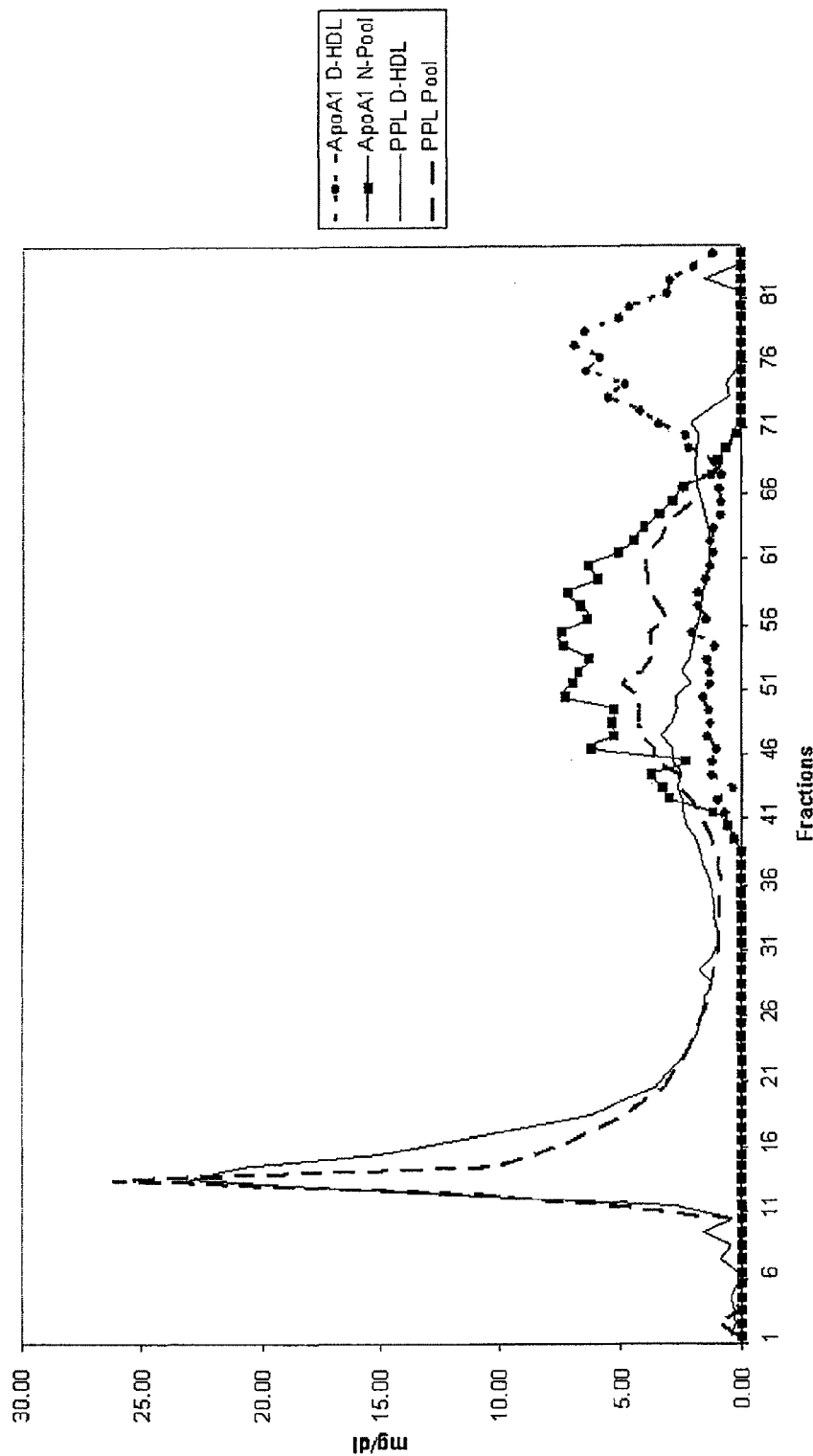
FIG. 5 is a schematic of an FPLC profile of an aliquot from the pool of normal plasma which was subjected to a solvent of 100% DIPE to remove lipid from HDL. Apo A-1 in the normal plasma sample from FIG. 3 is represented here as a solid line with square symbols. Apo A-1 in the normal plasma sample subjected to DIPE is shown as a dashed line with a dot symbol. Phospholipid (PPL) in the normal plasma sample from FIG. 3 is represented here with the dashed line. PPL in the normal plasma subjected to DIPE is shown as a solid line.
Figure 6:
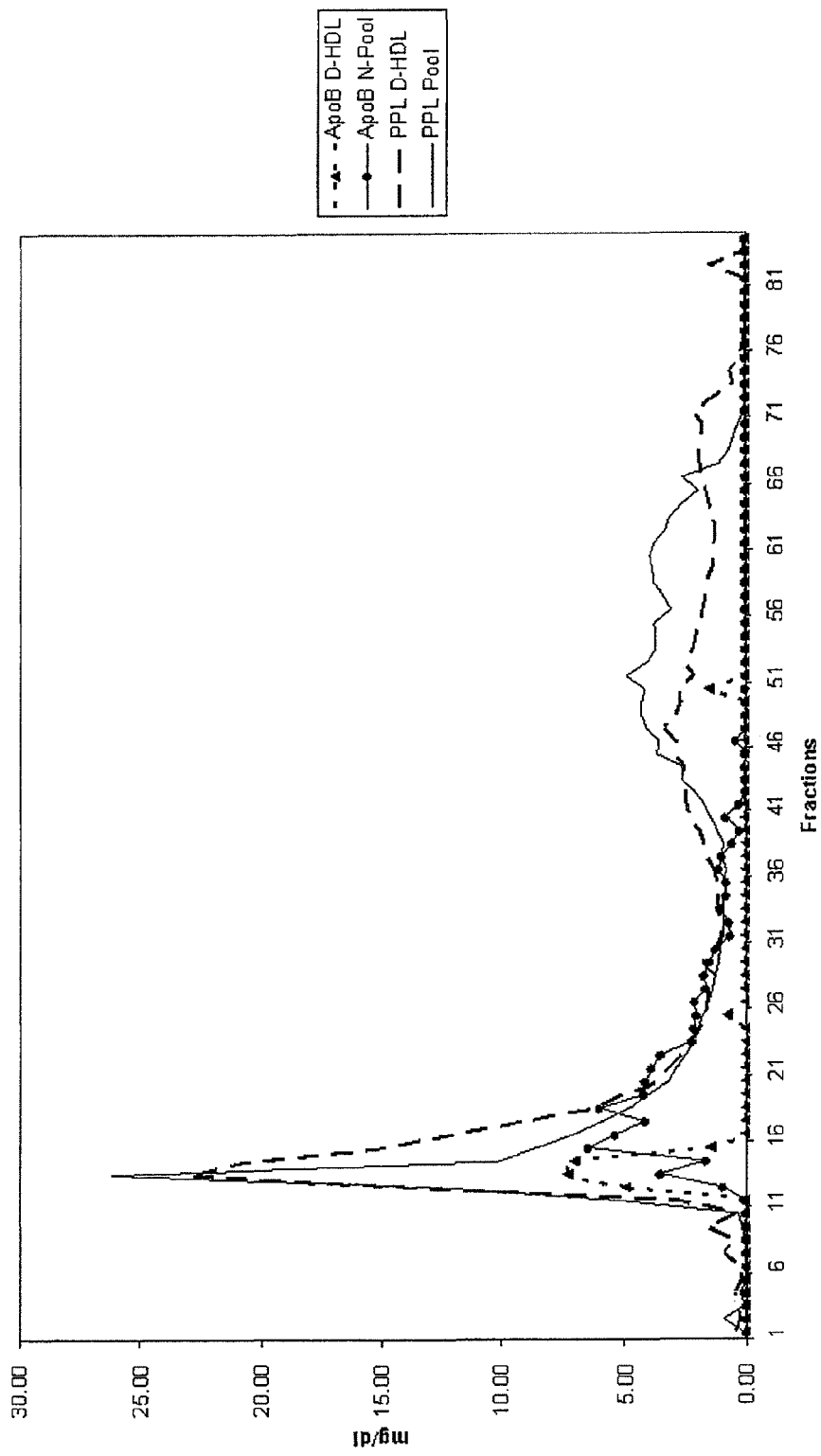
FIG. 6 is a schematic of an FPLC profile of an aliquot from the pool of normal plasma which was subjected to a solvent of 100% DIPE to remove lipid from HDL. Apo B in the normal plasma sample is represented by the line with a dot symbol. Apo B in the normal plasma subjected to DIPE is shown as dashed line with triangles. Phospholipid (PPL) in the normal sample from FIG. 3 is represented with the solid line. PPL in the normal plasma subjected to DIPE is shown as a dashed line.

A comparison of the elution of the delipidated sample with the elution of normal, non-delipidated plasma is presented in FIGS. 4 and 5. The results show a shift to the right of the Apo A-1-associated HDL particles, indicating a smaller particle not associated with cholesterol (FIG. 4) and also not associated with phospholipid (FIG. 5). Accordingly, this delipidation method created HDL particles associated with Apo A-1 that were low or substantially devoid of cholesterol and phospholipid and therefore had new capacity to bind with cholesterol and phospholipid. Lipid was only slightly removed from LDL particles (Apo B) with this method (FIG. 6).

In summary, two types of HDL particles were observed. There was a wide range of sizes of HDL particles containing Apo A-1 and phospholipids but no cholesterol. A relatively narrow size range of HDL particles containing Apo A-1 but no phospholipids or cholesterol was observed.

EXAMPLE 3

Selective Creation of Apo A-1-Associated HDL Particles with Reduced Cholesterol or with Reduced Cholesterol and Phospholipids Using a Sevoflurane:n-Butanol Mixture A mixture of sevoflurane and n-butanol was employed as a solvent in a concentration of 95% sevoflurane and 5% n-butanol. The mixture was added to plasma in a 2:1 solvent to plasma ratio. The sample was vortexed for 15 seconds and then centrifuged. Activated charcoal was added to remove residual solvent. The resulting solvent-free sample was run on an FPLC column as described in Example 1. Data concerning the percentage reduction in cholesterol, phospholipid and Apo A-1 were obtained from quantitative measurements and not from the FPLC elution profiles.

Figure 7:
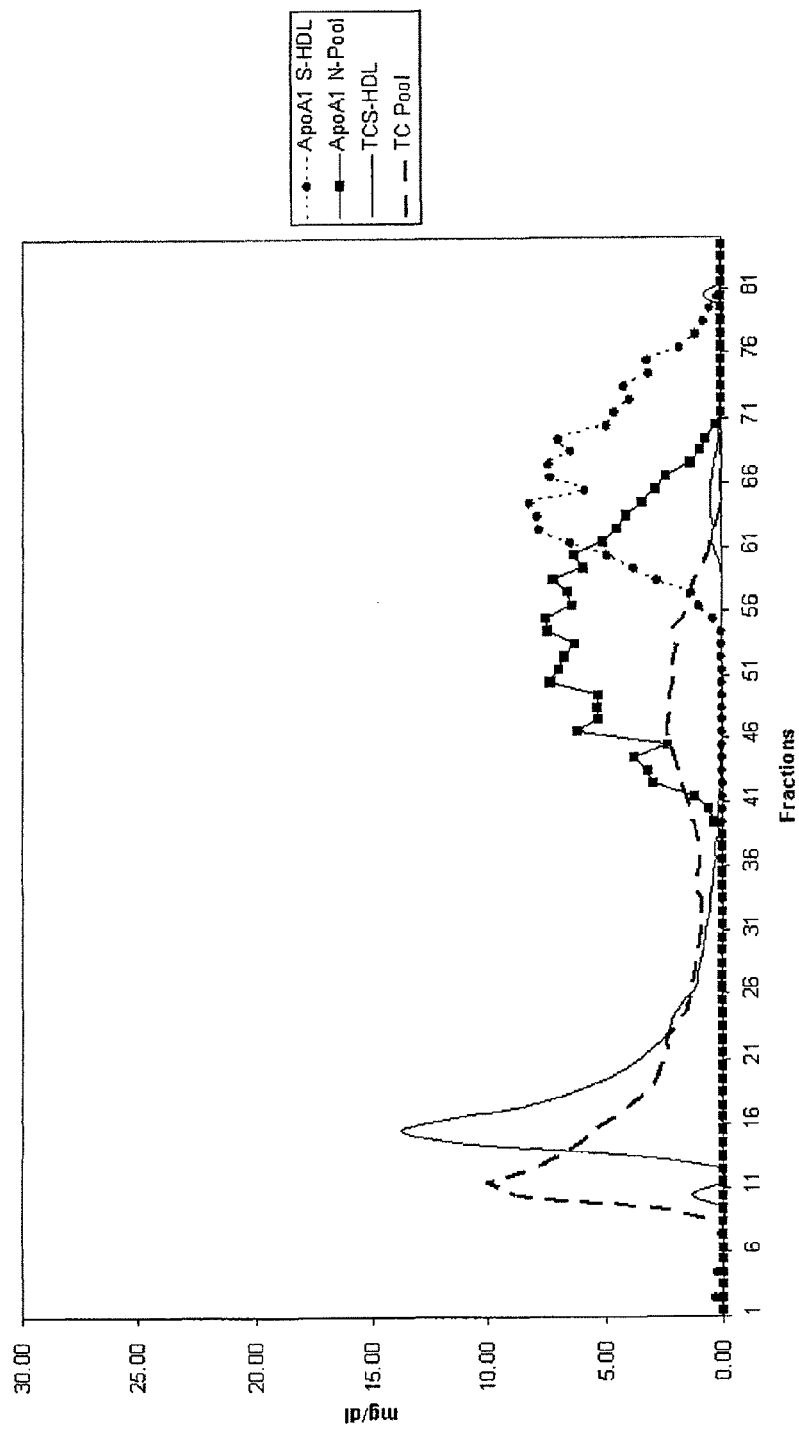
FIG. 7 is a schematic of an FPLC profile of an aliquot from the pool of normal plasma which was subjected to a solvent ratio of 95:5 sevoflurane to n-butanol. Total cholesterol (TC) in the normal plasma sample from FIG. 3 is represented here as a dashed line. TC in the normal plasma subjected to sevoflurane:n-butanol is shown as a solid line. Apo A-1 in the normal plasma sample from FIG. 3 is represented as a solid line with square symbols. Apo A-1 in the normal plasma subjected to sevoflurane:n-butanol is shown as a dashed line with a dot symbol.
Figure 8:
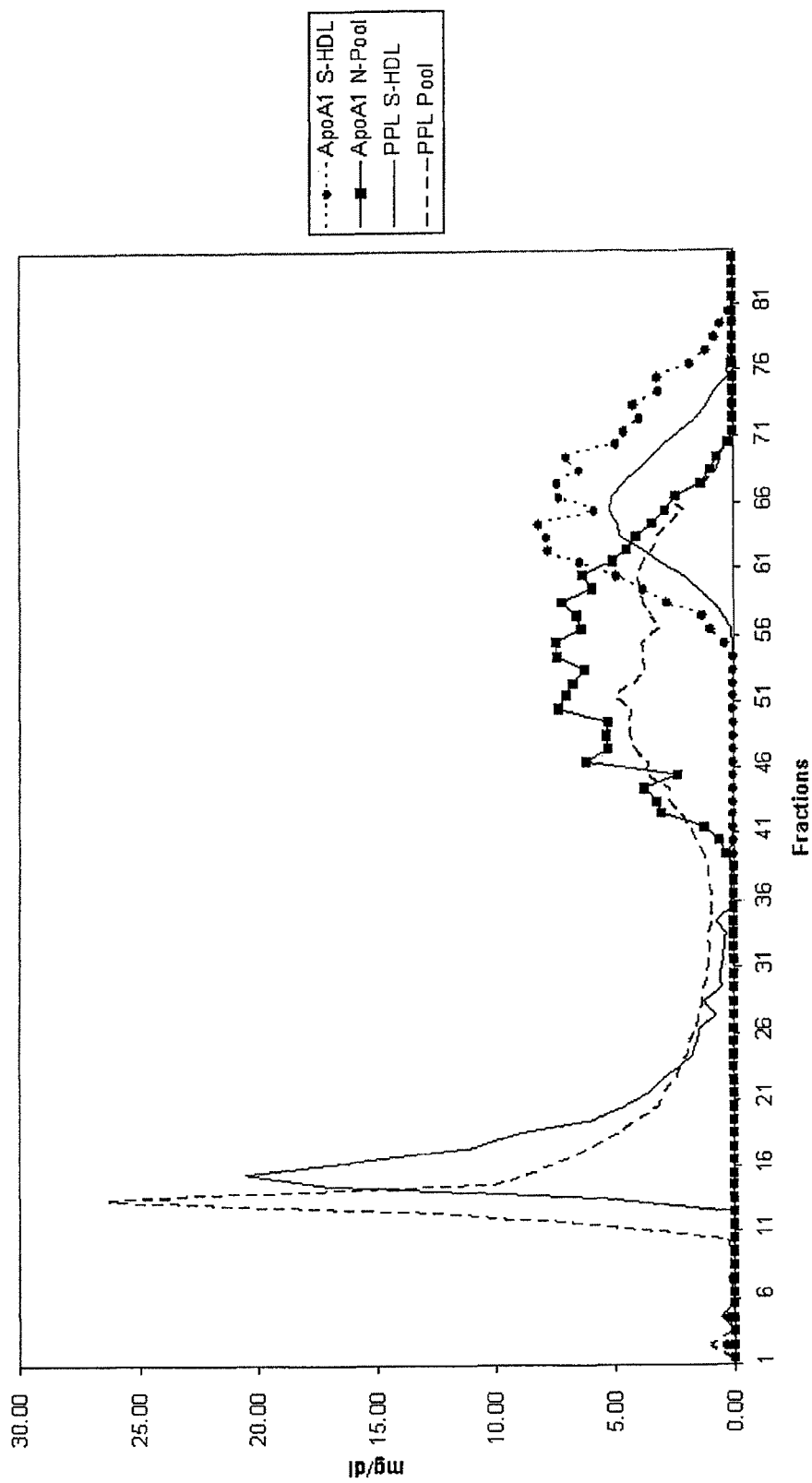
FIG. 8 is a schematic of an FPLC profile of an aliquot from the pool of normal plasma which was subjected to a solvent ratio of 95:5 sevoflurane to n-butanol. Apo A-1 in the normal sample from FIG. 3 is represented as a solid line with square symbols. Apo A-1 in the normal plasma subjected to sevoflurane:n-butanol is shown as a dashed line with a dot symbol. Phospholipid (PPL) in the normal sample from FIG. 3 is represented here with the dashed line. PPL in the normal plasma subjected to sevoflurane:n-butanol is shown as a solid line.
Figure 9:
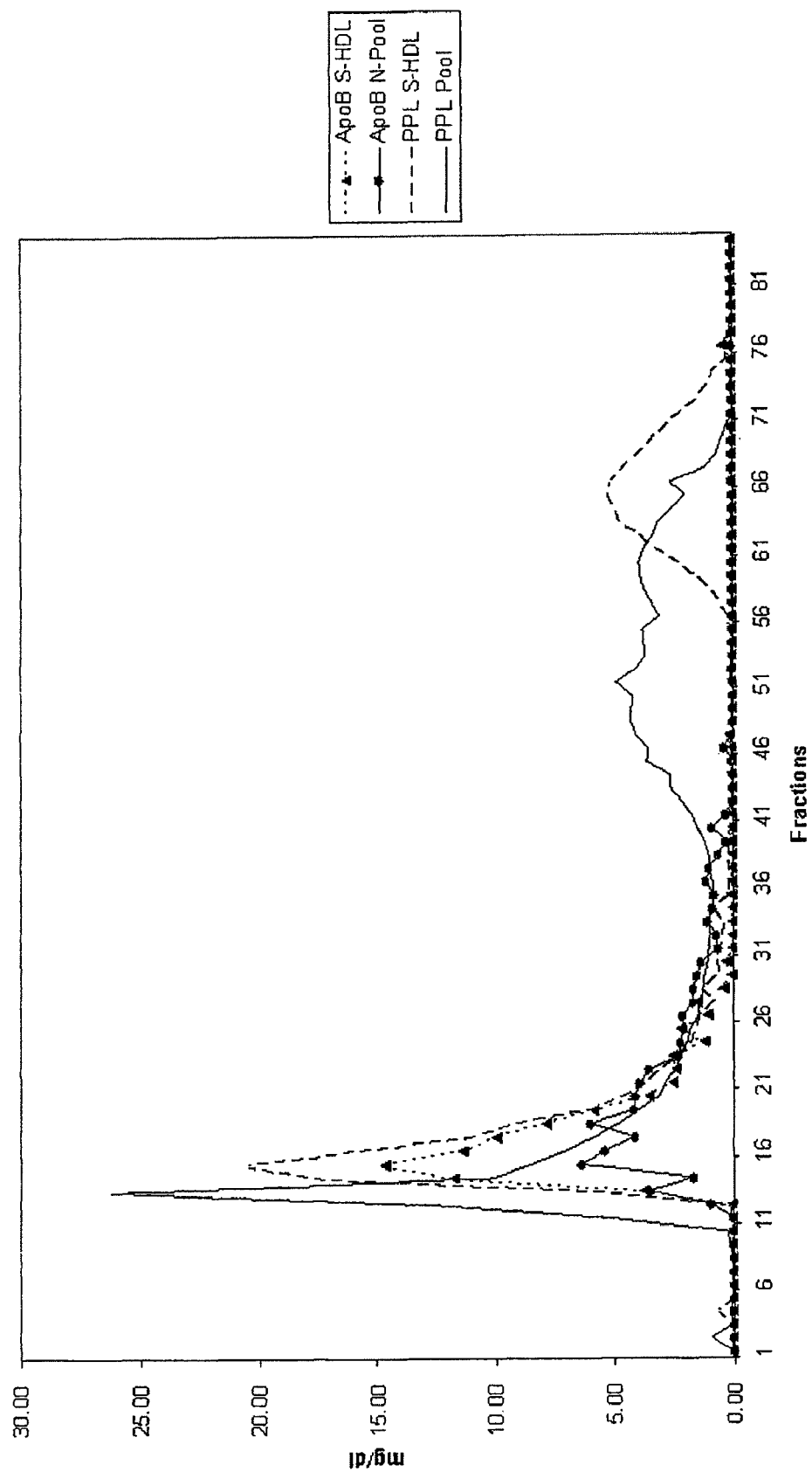
FIG. 9 is a schematic of an FPLC profile of an aliquot from the pool of normal plasma which was subjected to a solvent ratio of 95:5 sevoflurane to n-butanol. Apo B in the normal sample from FIG. 3 is represented by the line with a dot symbol. Apo B in the normal plasma subjected to sevoflurane:n-butanol is shown as dashed line with triangles. Phospholipid (PPL) in the normal sample from FIG. 3 is represented here with the solid line. PPL in the normal plasma subjected to sevoflurane:n-butanol is shown as a dashed line.

This method reduced total cholesterol by 9% and phospholipids by 9%. A decrease of about 14% was observed in Apo A-1. FIG. 7 shows that this method resulted in Apo A-1 associated HDL particles of lower weight that were not associated with cholesterol when compared to plasma that was not subjected to such treatment. However, these Apo A-1 associated HDL particles were associated with phospholipid (FIG. 8). There was little effect on Apo B associated LDL particles as shown in FIG. 9. In summary, this process resulted in a modified HDL particle which contained Apo A-1 and phospholipids, but little or no cholesterol.

EXAMPLE 4

Figure 10:
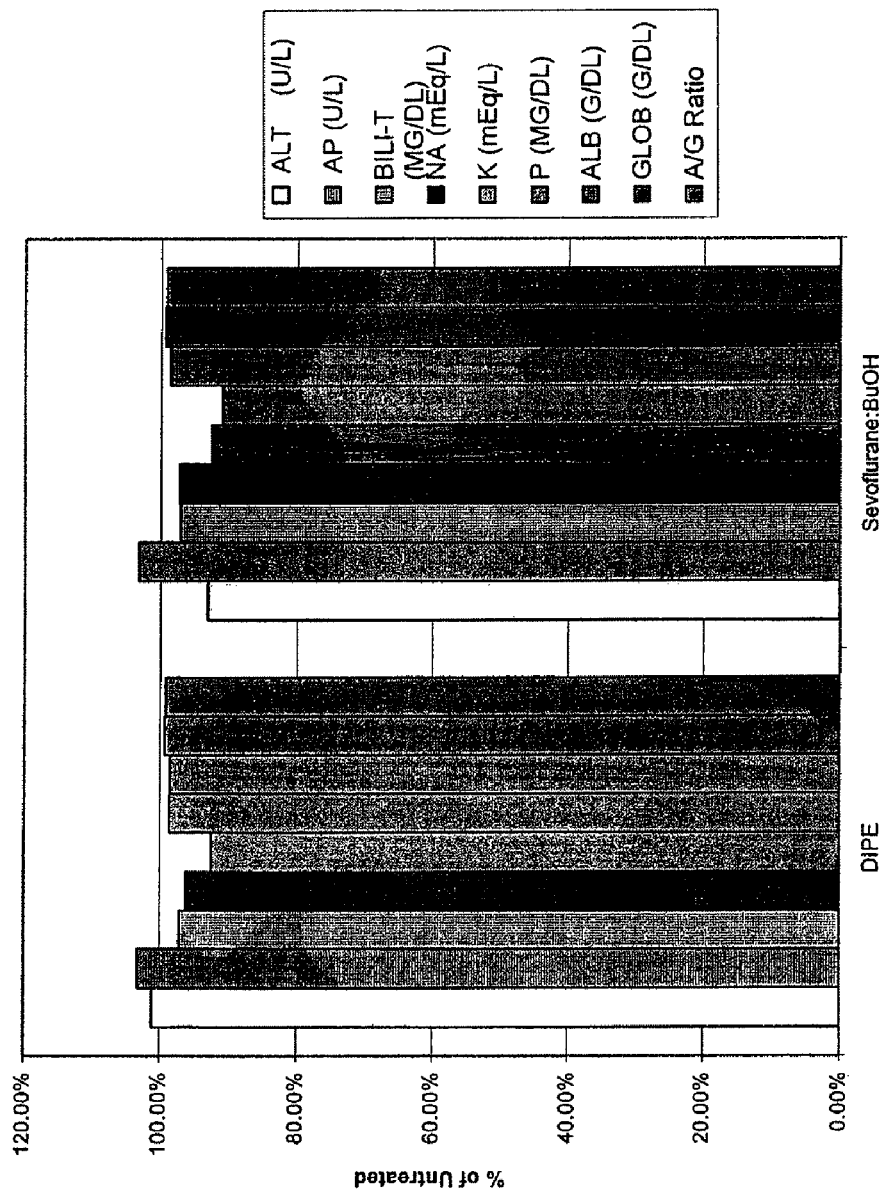
FIG. 10 is a schematic representation of the effect of treatment of a plasma sample with either DIPE or sevoflurane:butanol on alanine aminotransferase (ALT), alkaline phosphatase (AP), bilirubin-T, sodium, potassium, phosphorus, albumin, globulin and the albumin/globulin (A/G) ratio were analyzed in normal untreated plasma and in plasma treated with DIPE or with sevoflurane:n-butanol.

Analysis of Clinical Parameters in Normal Plasma and Plasma Treated with DIPE or Sevoflurane:n-Butanol Alanine aminotransferase (ALT), alkaline phosphatase (AP), bilirubin-T, sodium, potassium, phosphorus, albumin, globulin and the albumin/globulin (A/G) ratio were analyzed in normal untreated plasma and in plasma treated with 100% DIPE or with sevoflurane:n-butanol. The results are presented in FIG. 10.

Treatment with DIPE did not change the parameters to any clinically significant degree. Treatment with sevoflurane:n-butanol did not change the parameters to any clinically significant degree. These treatments, therefore, do not substantially affect non-HDL plasma constituent components.

EXAMPLE 5

Figure 11:
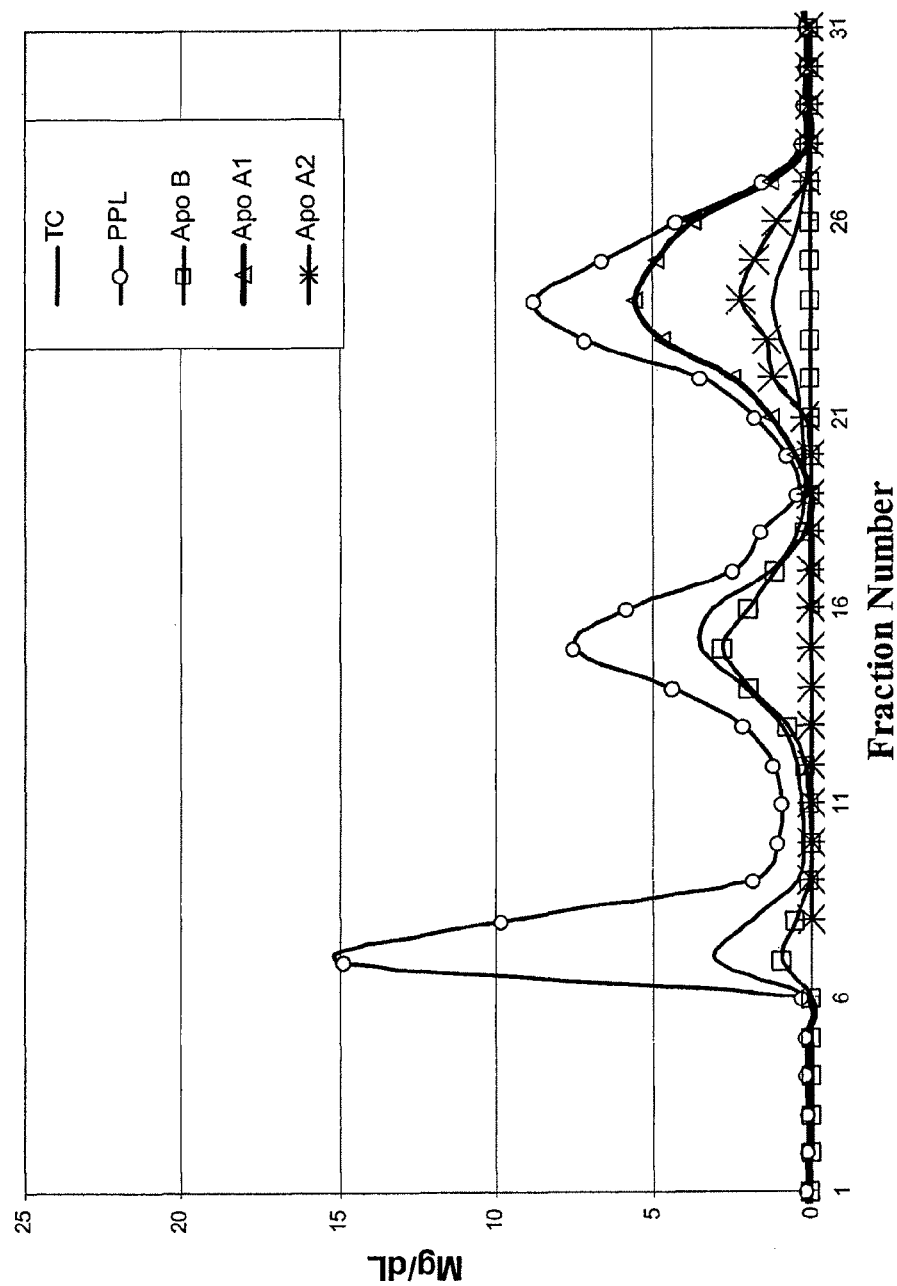
FIG. 11 is a schematic representation of a Superose FPLC profile of a normal plasma sample which acts as a control for comparison to the treatments in FIGS. 12-15. Total cholesterol (TC) in the normal plasma sample is represented here as a solid line. Phospholipid (PPL) is represented with the solid line with circles. Apo B is represented by the line with open squares. Apo A-1 is represented as a solid line with open triangle symbols. Apo A-2 is shown as a dashed line with a star symbol.
Figure 12:
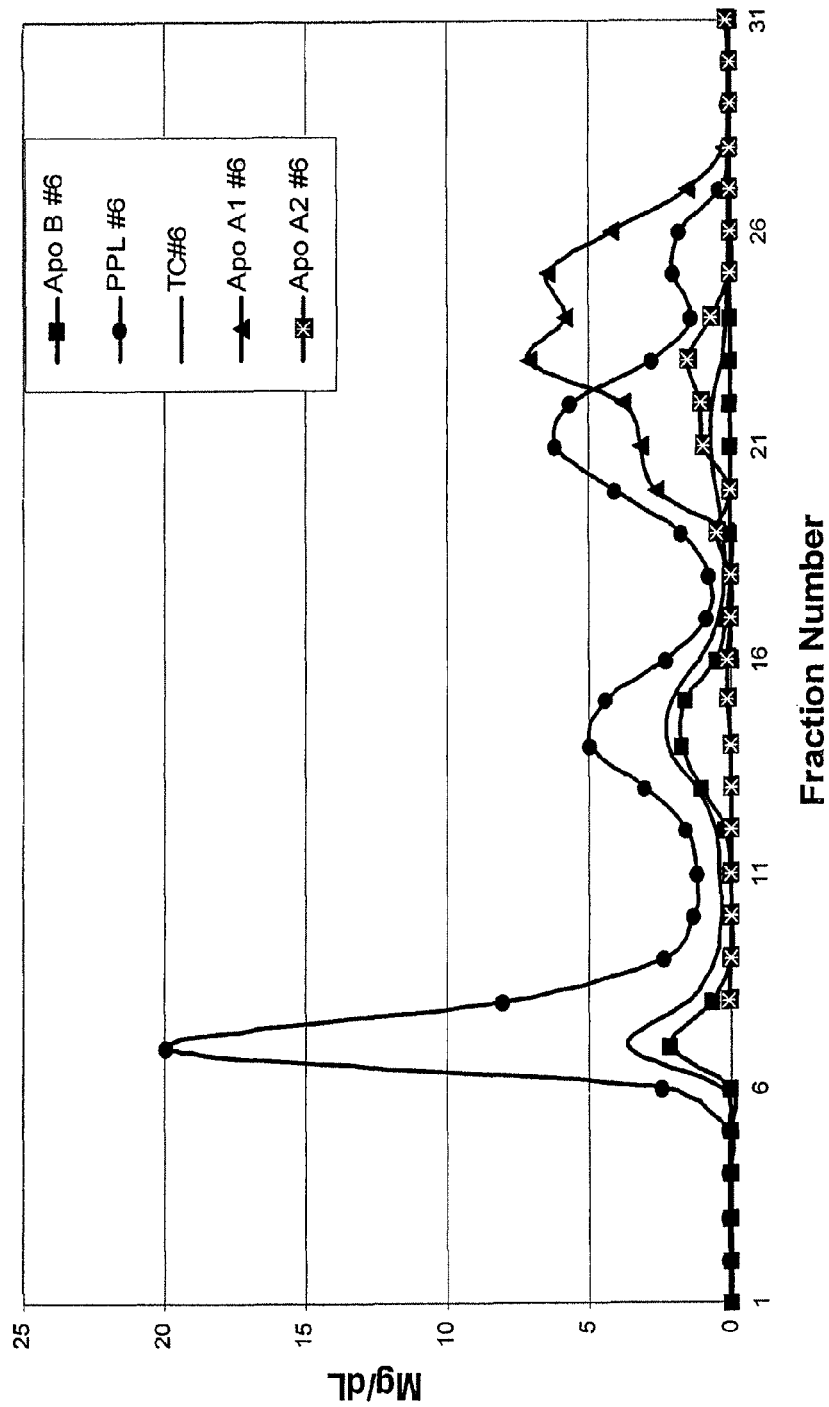
FIG. 12 is a schematic representation of a Superose FPLC profile of the effect of treatment of an aliquot of control plasma sample (FIG. 11) with DIPE (100%). Total cholesterol (TC) is represented here as a solid line. Phospholipid (PPL) is represented with the solid line with solid circles. Apo B is represented by the line with solid squares. Apo A-1 is represented as a solid line with closed triangle symbols. Apo A-2 is shown as a dashed line with a star symbol in a solid square.
Figure 13:
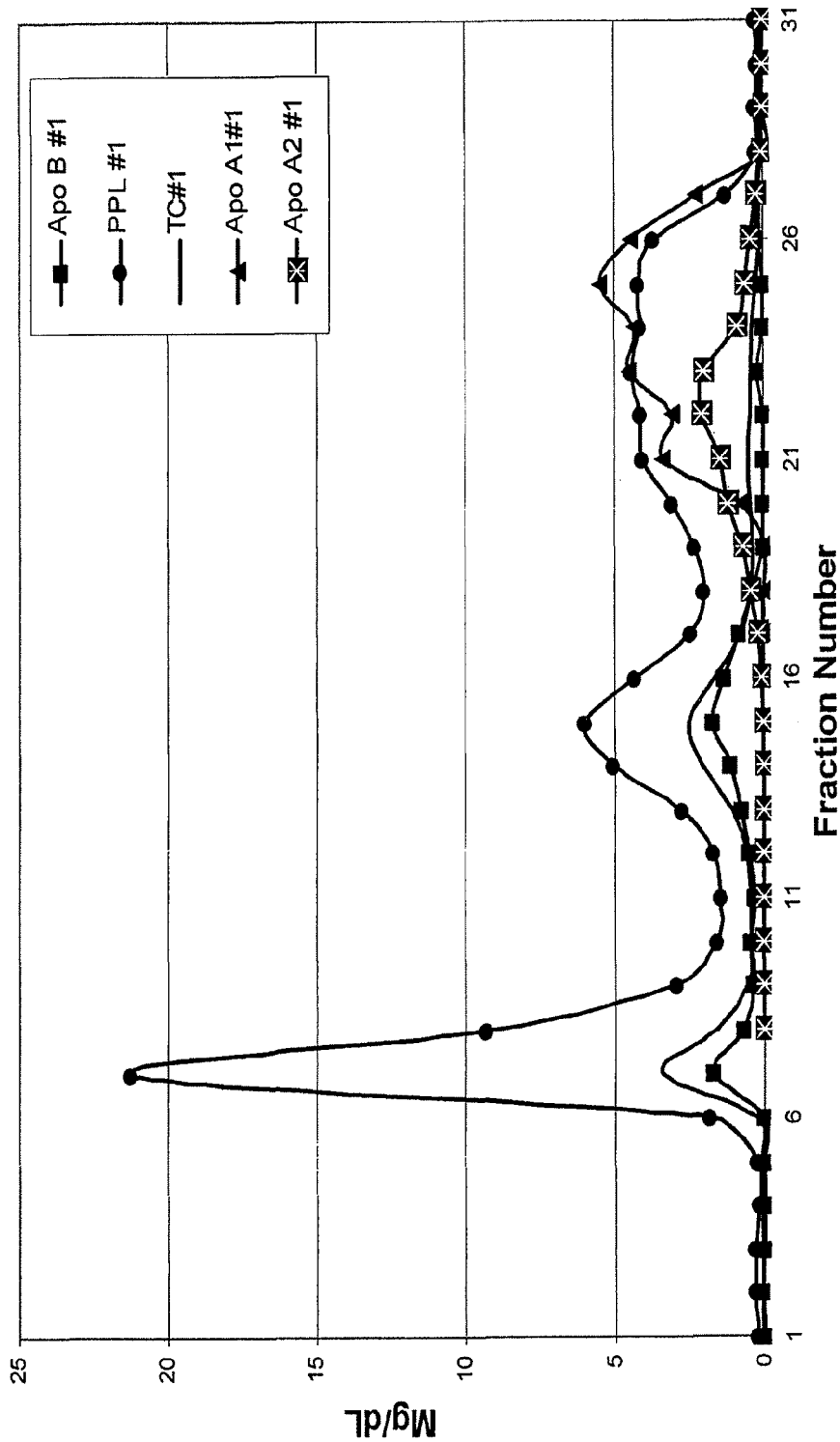
FIG. 13 is a schematic representation of a Superose FPLC profile of the effect of treatment of an aliquot of control plasma sample (FIG. 11) with a solvent ratio of 95:5 sevoflurane to n-butanol. Total cholesterol (TC) is represented here as a solid line. Phospholipid (PPL) is represented with the solid line with solid circles. Apo B is represented by the line with solid squares. Apo A-1 is represented as a solid line with closed triangle symbols. Apo A-2 is shown as a dashed line with a star symbol in a solid square.
Figure 14:
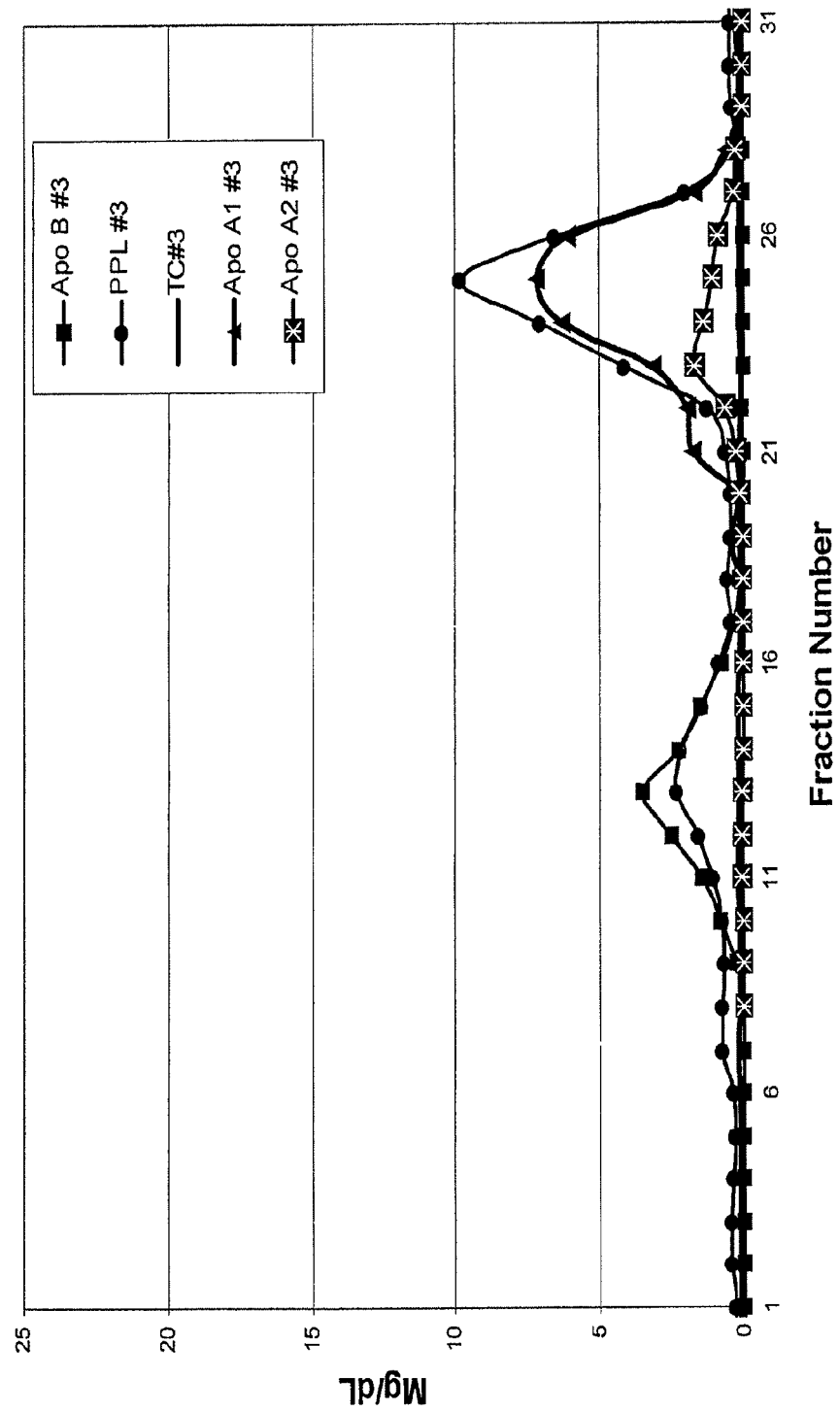
FIG. 14 is a schematic representation of a Superose FPLC profile of the effect of treatment of an aliquot of control plasma sample (FIG. 11) with a solvent ratio of 75:25 DIPE to n-butanol. Total cholesterol (TC) is represented here as a solid line. Phospholipid (PPL) is represented with the solid line with solid circles. Apo B is represented by the line with solid squares. Apo A-1 is represented as a solid line with closed triangle symbols. Apo A-2 is shown as a dashed line with a star symbol in a solid square.
Figure 15:
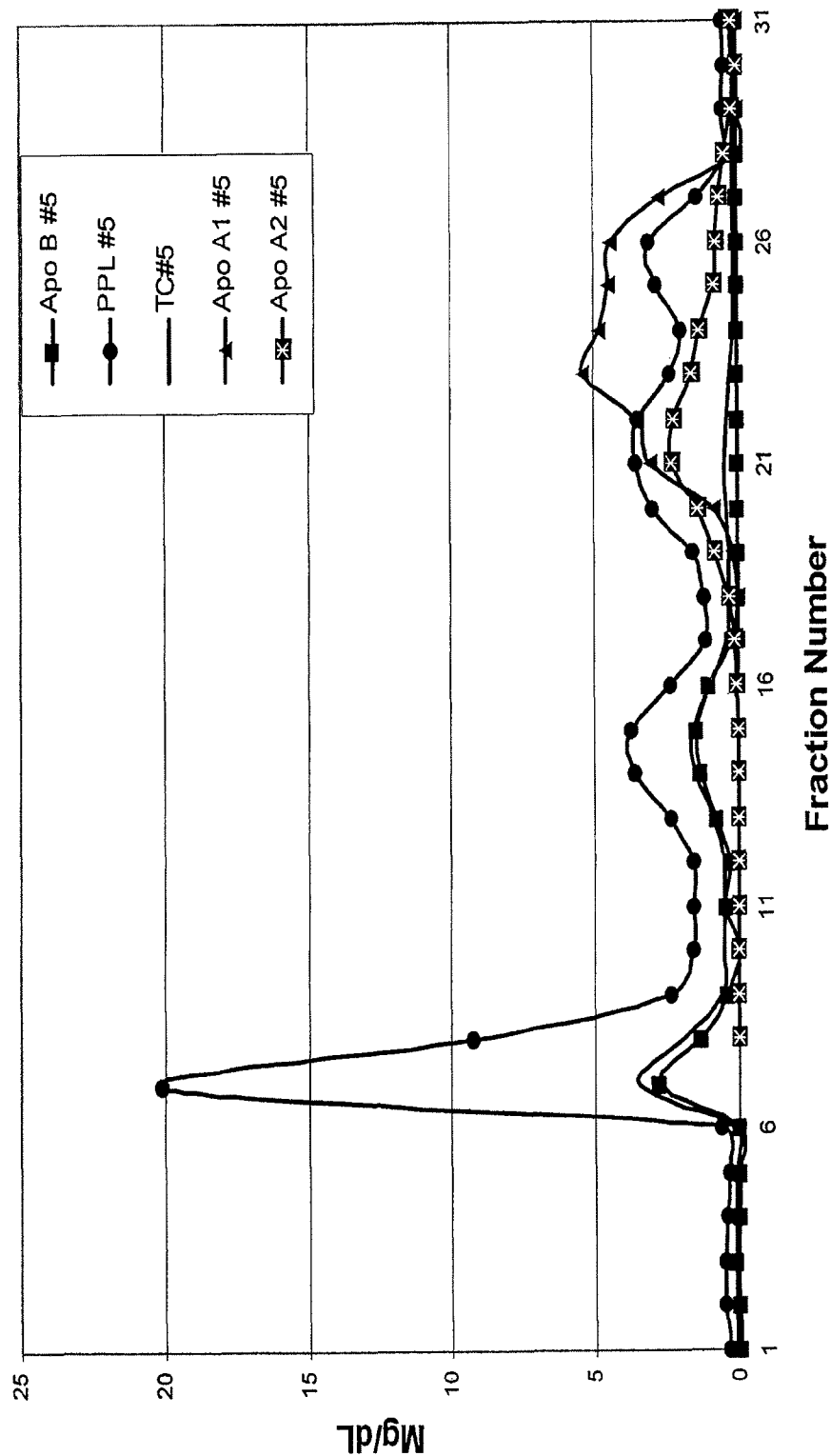
FIG. 15 is a schematic representation of a Superose FPLC profile of the effect of treatment of an aliquot of control plasma sample (FIG. 11) with a solvent ratio of 95:5 DIPE to n-butanol. Total cholesterol (TC) is represented here as a solid line. Phospholipid (PPL) is represented with the solid line with solid circles. Apo B is represented by the line with solid squares. Apo A-1 is represented as a solid line with closed triangle symbols. Apo A-2 is shown as a dashed line with a star symbol in a solid square.

Summary of the Efficacy of Different Solvents on Removal of Cholesterol from HDL and Effects on LDL FIGS. 11-15 show a Superose FPLC profile of plasma treated with nothing, DIPE (100%), sevoflurane:n-butanol (95:5), sevoflurane:n-butanol (75:25) and DIPE:n-butanol (95:5), respectively, for a variety of parameters. Shown are total cholesterol, phospholipid, Apo B, Apo A-1, and Apo A2. The data indicate that cholesterol is reduced following solvent treatment in the areas associated with Apo A-1 and Apo A2 (the peak on the right side of each figure) while the Apo B associated with LDL (middle peak) remains substantially unchanged. However, a severe solvent treatment with a solvent ratio of 75:25 DIPE:n-butanol (FIG. 14) dramatically reduced total cholesterol and phospholipids when compared to untreated plasma (FIG. 11).

EXAMPLE 6

Cholesterol Efflux Studies of Plasma Treated with Various Solvents

All solvent conditions above were employed to test the effects of treated plasma on cholesterol efflux in ABCA1 pathway and SRB1 pathway as measured in COS and Fu5AH cells. The methods employed were those described by Rothblatt and colleagues (de la Llera Moya et al., Arteriosclerosis. & Thrombosis 14:1056-1065, 1994).

The methods employed are described generally in the next paragraphs. The tissue culture cell system was designed to quantitate the contribution of scavenger receptor BI (SR-BI) or ATP-binding cassette transporter 1 (ABCA1) to the efflux of cellular cholesterol when cells are exposed to serum or isolated lipoproteins. The general approach is to measure the release of radiolabeled cellular cholesterol to either isolated acceptors or whole serum. The contributions of SR-BI or ABCA1 to this efflux process are determined by comparing the release obtained from cells lacking the specific receptor to that observed in parallel cell cultures expressing the receptor. Thus, to quantitate the contribution of ABCA1 to cellular cholesterol efflux, transformed mouse macrophage cells are grown in monolayers and prelabeled with $^3$H-cholesterol. One set of monolayers is treated with cAMP which has been shown to upregulate the ABCA1 receptor, whereas a replicate set of monolayers the are left untreated, and serve as control cells which lack ABCA1. The sera to be tested is diluted to an appropriate concentration and incubated with both ABCA1 positive and negative monolayers. The release of the radiolabeled cholesterol is determined after an appropriate incubation time ranging from 1 to 12 hours. The ABCA1-contribution to efflux is determined by subtracting the efflux obtained in ABCA1 negative cultures from that obtained from the ABCA1 positive cultures.

A general assay for determining the contribution of SRB1 to cholesterol efflux uses the same approach as described above. Cell lines serving as cholesterol donors are treated so that they either lack SRB1 or express high levels of the receptor. In the general protocol presently used COS-7 cells are transiently transfected when it SR-BI. These cells are prelabeled with 3H-cholesterol and then exposed to the test serum for appropriate periods of time. Following this period the medium is removed and a determination is made of the amount of radiolabeled cellular cholesterol that has been released. The efflux of cholesterol from control, SR-BI negative cells is subtracted from that observed with SR-BI expressing cells. The difference obtained by this calculation reflects the contribution of SR-BI to cholesterol efflux. An alternative cell system that can be used for determining SR-BI-mediated efflux is the Fu5AH rat hepatoma cell. These cells expresses very high levels of SR-BI and the efflux of radiolabeled cholesterol from Fu5AH is a very reliable measure of the contribution of SR-BI to the efflux process.

Figure 16:
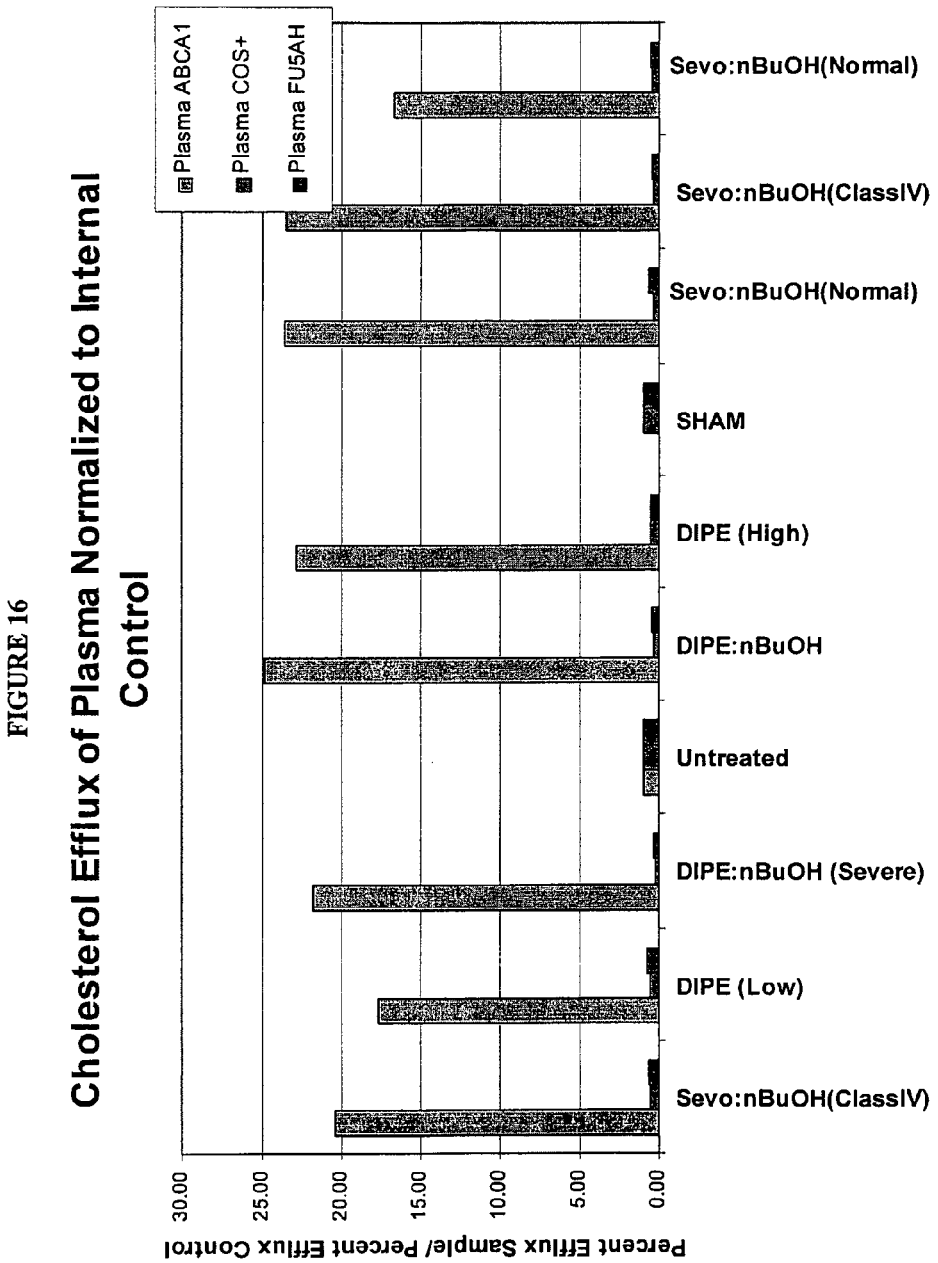
FIG. 16 demonstrates the effects of various solvent treatments of plasma on the ability of treated plasma to stimulate cholesterol efflux in metabolic pathway ABCA1 and metabolic pathway SRB1 as represented in cell lines COS+ and FU5AH when compared to untreated or sham treated samples.

The results are shown in FIG. 16 and demonstrate that plasma treated with the various solvents stimulated efflux of cholesterol 20 to 25 times more efficiently than untreated or sham treated plasma, taken from the same pool of starting plasma. This effect was observed in ABCA1 cells, which possess a metabolic pathway believed to be representative of cholesterol egress from arterial walls, but not in COS+ or FU5AH cells which are believed to be representative of the SRB1 pathway in the liver. Further testing of sevoflurane:n-butanol of three different plasma samples obtained from different individuals produced similar results (FIG. 16, set of histograms). By creating a modified HDL particle, the present invention therefore positively affects the effectiveness of the SRB1 and ABCA1 pathways. The present invention also encompasses the modification of SRB1 and ABCA1 pathways by modifying the relative ratio of phospholipid to Apo A-1 in HDL particles via the above described delipidation processes.

EXAMPLE 7

Analysis of Solvent Treatment on Levels of Apo A-1 Associated Pre B-2 HDL and pre B-1 HDL Particles The individual effects of sevoflurane:n-butanol and DIPE:n-butanol (95:5) on Apo A-1-containing HDL subspecies were examined using 3-16% native PAGE gels, followed by immunoblotting and image analysis. The techniques employed are described in Asztalos et al., Arteriosclerosis, Thrombosis and Vascular Biology; 15:1419-1423, 1995 and Asztalos et al., Arteriosclerosis, Thrombosis and Vascular Biology; 17:1885-1893, 1997.

Figure 17:
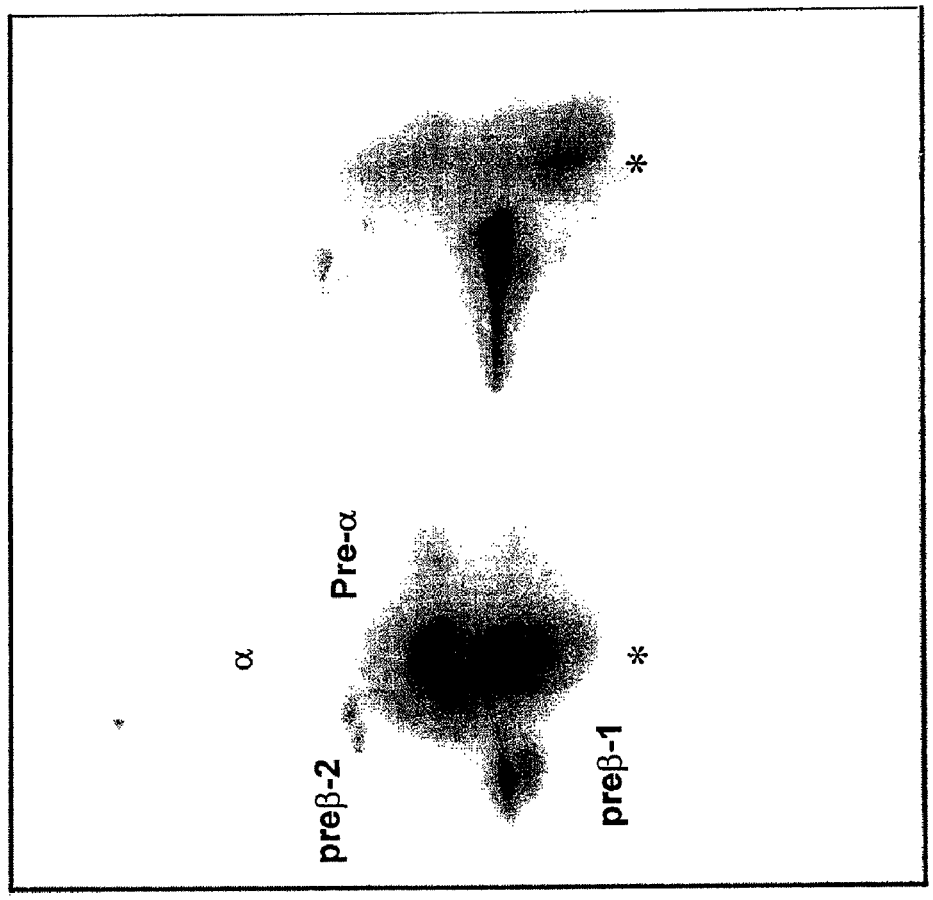
FIG. 17 is a representation of Apo A-1-containing HDL subspecies determined by 3-16% native PAGE, immunoblot and image analysis of a sample of normal lipemic plasma (left panel) and an aliquot of this plasma treated with sevoflurane:n-butanol (95:5) (right panel). The left panel depicts a distribution of protein of various HDL species having a distribution primarily comprising alpha HDL and the right panel depicts a distribution of protein of modified HDL having a distribution primarily comprising pre-β HDL.
Figure 18:
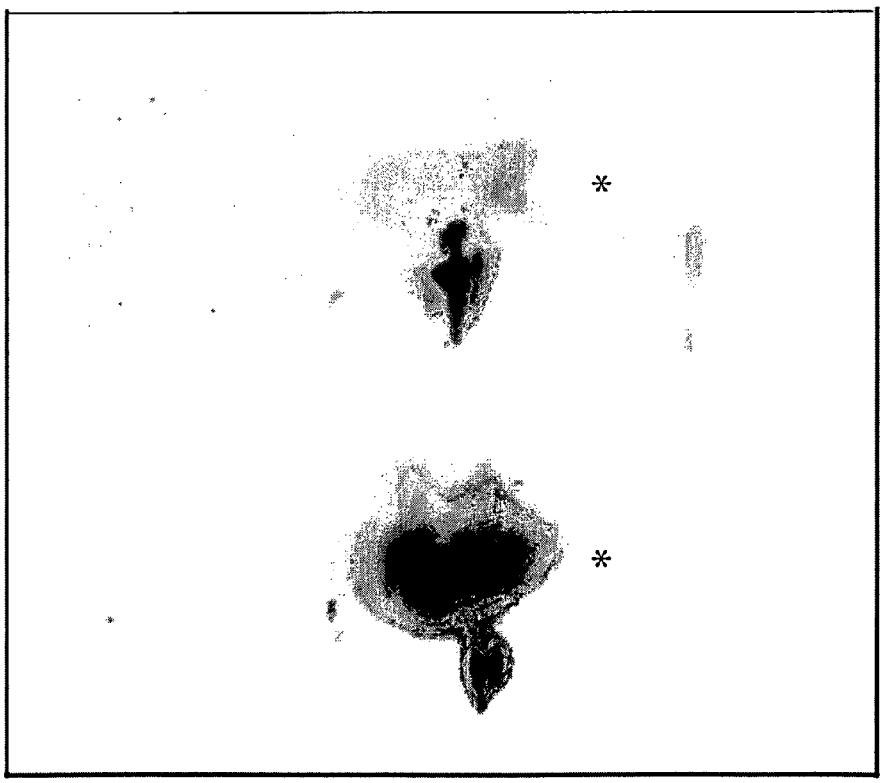
FIG. 18 is a representation of Apo A-1-containing HDL subspecies determined by 3-16% native PAGE, immunoblot and image analysis of a sample of normal lipemic plasma (left panel) and a aliquot of this plasma treated with DIPE:n-butanol (95:5) (right panel). The left panel depicts a distribution of protein of various HDL species having a distribution primarily comprising alpha HDL and the right panel depicts a distribution of protein of modified HDL having a distribution primarily comprising pre-β HDL.

The left side of FIGS. 17 and 18 each show Apo A-1-containing HDL subspecies, namely preβ-2, preβ-1, α and pre-α particles in normal lipemic plasma, while the right panel of each figure shows normal plasma treated with sevoflurane:n-butanol and DIPE:n-butanol (95:5) FIG. 17 demonstrates that plasma treated with sevoflurane:n-butanol showed an increase in the Apo A-1-containing preβ-2, preβ-1 HDL subspecies and a decrease in the α HDL subspecies. A similar pattern was observed following treatment with DIPE:n-butanol (FIG. 18). These results demonstrate that these solvent treatments of plasma increased Apo A-1-containing preβ-2, preβ-1 HDL subspecies, thereby enhancing their availability for accepting new cholesterol and facilitating cellular cholesterol efflux.

A similar comparison of the untreated normal plasma shown in the left panel of FIGS. 17 and 18 and another untreated plasma sample with slightly elevated cholesterol levels produced a similar pattern (data not shown) with most of the immunoreactive HDL species appearing in the αHDL form with relatively minor density associated with preβ-2 and preβ-1 HDL particles. These results provide an internal methodological control.

EXAMPLE 8

Administration of Derivatives of HDL to a Patient with Elevated Cholesterol and Coronary Artery Disease A 51 year old male patient presents with acute coronary syndrome and is determined to have atherosclerosis via angiography. A unit of blood is removed weekly from the patient. The plasma is recovered and processed with the method of the present invention to produce derivatives of HDL that are particles with reduced cholesterol content while the red blood cells are returned to the patient. These HDL particles with reduced cholesterol content in the treated plasma are administered to the patient intravascularly at weekly intervals for 5-10 weeks. Another angiography test after completion of the treatment shows lower amounts of atherogenic plaque in the coronary vessels compared to the first angiography test.

EXAMPLE 9

Administration of Derivatives of HDL Together with Atorvastatin and Ezetimibe to a Patient with Elevated Cholesterol and Coronary Artery Disease A 58 year old female presents with acute coronary syndrome and is determined to have atherosclerosis via angiography. A unit of blood is removed weekly from the patient. The plasma is recovered and processed with the method of the present invention to produce derivatives of HDL that are particles with reduced cholesterol content while the red blood cells are returned to the patient. These HDL particles with reduced cholesterol content in the treated plasma are administered to the patient intravascularly at weekly intervals for 5-10 weeks. The patient had previously received 80 mg of atorvastatin daily with 10 mg of ezetimibe. These drugs are continued daily together with the weekly administration of HDL particles with reduced cholesterol content. Another angiography test after completion of the treatment shows lower amounts of atherogenic plaque in the coronary vessels compared to the first angiography test.

EXAMPLE 10

Administration of Derivatives of HDL Together with Simvastatin and Ezetimibe to an Obese Patient with Elevated Cholesterol and Coronary Artery Disease A 48 year old obese female patient presents with elevated levels of LDL and cholesterol, and an angiographic test result indicating atherosclerosis in three coronary arteries. A unit of blood is removed weekly from the patient. The plasma is recovered and processed with the method of the present invention to produce derivatives of HDL that are particles with reduced cholesterol content while the red blood cells are returned to the patient. These HDL particles with reduced cholesterol content are combined with the treated plasma and administered to the patient intravascularly at weekly intervals for 5-10 weeks. The patient had previously received 80 mg of simvastatin daily with 10 mg of ezetimibe. These drugs are continued daily together with the weekly administration of HDL particles with reduced cholesterol content. The patient is placed on a moderate exercise schedule.

New blood work indicates a reduction in circulating cholesterol, a reduction in LDL and an increase in circulating HDL. The patient loses 15 pounds during the five month period. A new angiographic procedure shows lower amounts of atherogenic plaque in the coronary vessels compared to the first angiographic procedure.

EXAMPLE 11

Administration of Derivatives of HDL to a Diabetic Patient with Elevated Cholesterol and Coronary Artery Disease A 44 year old diabetic female patient presents with elevated levels of LDL and cholesterol, and an angiographic test result indicating atherosclerosis in two coronary arteries. A unit of blood is removed weekly from the patient. The plasma is recovered and processed with the method of the present invention to produce derivatives of HDL that are particles with reduced cholesterol content while the red blood cells are returned to the patient. These HDL particles with reduced cholesterol content are combined with the treated plasma and administered to the patient intravascularly at weekly intervals for 5-10 weeks. The patient had previously received daily insulin injections. These injections are continued daily together with the weekly administration of HDL particles with reduced cholesterol content.

New blood work indicates a reduction in circulating cholesterol, a reduction in LDL and an increase in circulating HDL. A new angiographic procedure shows lower amounts of atherogenic plaque in the coronary vessels compared to the first angiographic procedure.

EXAMPLE 12

Administration of Derivatives of HDL to a Patient with Elevated Cholesterol and Peripheral Vascular Disease Causing Intermittent Claudication A 66 year old male patient presents with elevated levels of LDL and cholesterol and reports pain in the right lower extremity. An angiographic test indicating atherosclerosis in the right popliteal and posterior tibial arteries, leading to a diagnosis of intermittent claudication. A unit of blood is removed weekly from the patient. The plasma is recovered and processed with the method of the present invention to produce derivatives of HDL that are particles with reduced cholesterol content while the red blood cells are returned to the patient. These HDL particles with reduced cholesterol content are combined with the treated plasma and administered to the patient intravascularly at weekly intervals for 5-10 weeks.

New blood work indicates a reduction in circulating cholesterol, a reduction in LDL and an increase in circulating HDL. A new angiographic procedure shows lower amounts of atherogenic plaque in the right popliteal and posterior tibial arteries compared to the first angiographic procedure. The patient reports decreased levels of pain from the right lower extremity.

All patents, publications and abstracts cited above are incorporated herein by reference in their entirety. The terms and expressions which have been employed herein are used as terms of description and not of limitation, and there is no intention, in the use of such terms and expressions, of excluding any equivalents of the features shown and described or portions thereof. It should be understood that the foregoing relates only to preferred embodiments of the present invention and that numerous modifications or alterations may be made therein without departing from the spirit and the scope of the present invention as defined in the following claims.

The invention claimed is:

1. A method of modifying a protein distribution in a fluid, wherein the protein distribution has a first state, the first state having alpha high density lipoproteins and pre-beta high density lipoproteins, comprising the steps of:
exposing the fluid to a lipid removing agent wherein the exposure modifies the protein distribution from the first state into a second state, the second state having an increased concentration of pre-beta high density lipoproteins relative to the first state; and,
removing the lipid removing agent from the fluid, wherein the lipid removing agent comprises sevoflurane.

2. The method of claim 1, wherein the fluid is plasma.

3. The method of claim 1, wherein the lipid removing agent comprises at least one of an ether, di-isopropyl ether, alcohol, or n-butanol.

4. The method of claim 1, wherein the lipid removing agent is a mixture of sevoflurane and n-butanol.

5. The method of claim 1, wherein the fluid comprises low density lipoproteins prior to exposing the fluid to the lipid removing agent.

6. The method of claim 5, wherein the low density lipoproteins are not removed from the fluid prior to exposing the fluid to the lipid removing agent.

7. The method of claim 6, wherein the fluid is exposed to the lipid removing agent using an extracorporeal process, wherein the fluid exposure leaves low density lipoproteins substantially unmodified as compared to the low density lipoproteins in the fluid prior to exposure of the fluid to the lipid removing agent.

8. The method of claim 7, wherein the extracorporeal process transforms at least some of the alpha high density lipoproteins into pre-beta high density lipoproteins.

9. The method of claim 8, wherein the pre-beta high density lipoproteins transformed from the alpha high density lipoproteins have a lower cholesterol content than the alpha high density lipoproteins.

10. The method of claim 1, wherein the low density lipoproteins are not in the fluid when the fluid is exposed to the lipid removing agent.

11. The method of claim 10, wherein the exposure of the fluid to the lipid removing agent transforms at least some of the alpha high density lipoproteins into pre-beta high density lipoproteins.

12. The method of claim 11, wherein the pre-beta high density lipoproteins transformed from the alpha high density lipoproteins have a lower cholesterol content than the alpha high density lipoproteins.

13. The method of claim 10, wherein the low density lipoproteins are removed from the fluid prior to exposing the fluid to the lipid removing agent using an extracorporeal process.

14. The method of claim 1, wherein the first state has more alpha high density lipoproteins than pre-beta high density lipoproteins.

15. The method of claim 14, wherein the second state has more pre-beta high density lipoproteins than alpha high density lipoproteins.

16. The method of claim 1, wherein the fluid with the modified protein distribution is administered to a patient.

17. The method of claim 16, wherein the fluid with the modified protein distribution is autologous to the patient.

18. The method of claim 16, wherein the fluid with the modified protein distribution is not autologous to the patient.

19. The method of claim 1, wherein the fluid is a biological fluid.

20. A method of modifying a protein distribution in a fluid, wherein the protein distribution has a first state, the first state having more alpha high density lipoproteins than pre-beta high density lipoproteins, comprising the steps of:
    exposing the fluid to a lipid removing agent wherein the exposure modifies the protein distribution from the first state into a second state, the second state having more pre-beta high density lipoproteins than alpha high density lipoproteins; and,
    removing the lipid removing agent from the fluid,
    wherein the lipid removing agent comprises sevoflurane.

21. The method of claim 20, wherein Apolipoprotein B (ApoB) proteins associated with low density lipoproteins are in the fluid.

22. The method of claim 21, wherein the ApoB proteins are substantially unaffected by the lipid removing agent.

23. The method of claim 20, wherein the fluid is plasma.

24. The method of claim 20, wherein the fluid is a biological fluid.

* * * * *